US009243239B2

(12) United States Patent
Carrillo et al.

(10) Patent No.: US 9,243,239 B2
(45) Date of Patent: Jan. 26, 2016

(54) PURIFICATION OF CYSTATHIONINE BETA-SYNTHASE

(71) Applicant: The Regents of the University of Colorado, a body corporate, Denver, CO (US)

(72) Inventors: Richard Carrillo, Oakland, CA (US); Jan P. Kraus, Littleton, CO (US); Tomas Majtan, Aurora, CO (US); David Naveh, Piedmont, CA (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 13/830,494

(22) Filed: Mar. 14, 2013

(65) Prior Publication Data
US 2013/0251700 A1   Sep. 26, 2013

Related U.S. Application Data

(60) Provisional application No. 61/615,629, filed on Mar. 26, 2012.

(51) Int. Cl.
*C12N 9/88* (2006.01)
(52) U.S. Cl.
CPC ........... *C12N 9/88* (2013.01); *C12Y 402/01022* (2013.01)
(58) Field of Classification Search
CPC .......................... C12N 9/88; C12Y 402/01022
See application file for complete search history.

(56) References Cited

U.S. PATENT DOCUMENTS

| 5,523,225 | A  |    | 6/1996  | Kraus |
| 5,635,375 | A  |    | 6/1997  | Kraus et al. |
| 7,485,307 | B2 |    | 2/2009  | Kraus et al. |
| 7,816,495 | B2 | *  | 10/2010 | Kingsland et al. ............ 530/382 |
| 8,007,787 | B2 |    | 8/2011  | Kraus |

FOREIGN PATENT DOCUMENTS

| EP | 1396537 A1    | 3/2004  |
| EP | 1878739 A1    | 1/2008  |
| WO | 9507714 A1    | 3/1995  |
| WO | 03106971 A2   | 12/2003 |
| WO | 2011097381 A2 | 8/2011  |

OTHER PUBLICATIONS

International Search Report from International Application No. PCT/US2013/033716 mailed on Jun. 21, 2013.
Belew et al., "Kinetic characterization of recombinant human cystathionine beta-synthase purified from *E. coli*," Protein Expression and Purification, 64(2):139-45 (2009).
Frank et al., "Purification and characterization of the wild type and truncated human cystathionine beta-synthase enzymes expressed in *E. coli*," Archives of Biochemistry and Biophysics, 470(1):64-72 (2007).
Vozdek et al., "Novel structural arrangement of nematode cystathionine [beta]-synthases: characterization of Caenorhabditis elegans CBS-1," Biochemical Journal, 16(2)1066-547 (2012).
Bateman, 1997, "The structure of a domain common to archaebacteria and the homocystinuria disease protein." Trends Biochem. Sci. 22(1):12-13.
Finkelstein & Martin, 1984, "Methionine metabolism in mammals. Distribution of homocysteine between competing pathways." J. Biol. Chem. 259:9508-13.
Finkelstein et al., 1975, "Activation of cystathionine synthase by adenosylmethionine and adenosylethionine." Biochem. Biophys. Res. Commun. 66:81-87.
Jakubowski et al., 2008, "Mutations in cystathionine beta-synthase or methylenetetrahydrofolate reductase gene increase N-homocysteinylated protein levels in humans." FASEB J 22(12): 4071-6.
Janosik et al., 2001, "Regulation of human cystathionine beta-synthase by S-adenosyl-L-methionine: evidence for two catalytically active conformations involving an autoinhibitory domain in the C-terminal region." Biochemistry 40:10625-33.
Kery et al., 1998, "Trypsin cleavage of human cystathionine beta-synthase into an evolutionarily conserved active core: structural and functional consequences." Arch. Biochem. Biophys. 355:222-32.
Kozich & Kraus, 1992, "Screening for mutations by expressing patient cDNA segments in *E. coli*: homocystinuria due to cystathionine beta-synthase deficiency." Hum. Mutation 1:113-23.
Kraus, 1987, "Cystathionine beta-synthase (human)." Methods Enzymol. 143:388-94.
Lowry et al., 1951, "Protein measurement with the Folin phenol reagent." J. Biol. Chem. 193(1):265-75.
Maclean et al., 2002, "High homocysteine and thrombosis without connective tissue disorders are associated with a novel class of cystathionine beta-synthase (CBS) mutations." Hum. Mutat. 19(6):641-55.
Miles & Kraus, 2004, "Cystathionine beta-synthase: structure, function, regulation, and location of homocystinuria-causing mutations." J. Biol. Chem. 279(29):29871-4.
Roper & Kraus, 1992, "Rat cystathionine beta-synthase: expression of four alternatively spliced isoforms in transfected cultured cells." Arch. Biochem. Biophys. 298(2):514-21.
Shan et al., 2001, "Mutations in the regulatory domain of cystathionine beta synthase can functionally suppress patient-derived mutations in cis." Hum. Mol. Genet. 10(6):635-43.
Vargas et al., 1993, "Detection of c-type cytochromes using enhanced chemiluminescence." Anal. Biochem. 209 (2):323-6.

(Continued)

*Primary Examiner* — Robert Yamasaki
*Assistant Examiner* — Teresa E Knight
(74) *Attorney, Agent, or Firm* — McDonnell Boehnen Hulbert & Berghoff LLP

(57) ABSTRACT

This invention provides chromatographic methods for the purification of a cystathionine β-Synthase (CBS) protein, particularly truncated variants thereof and compositions and pharmaceutical compositions prepared therefrom.

19 Claims, 14 Drawing Sheets

(56) References Cited

OTHER PUBLICATIONS

Wilcken et al., 1983, "Homocystinuria—the effects of betaine in the treatment of patients not responsive to pyridoxine." N. Engl. J. Med. 309(8):448-53.

International Preliminary Report on Patentability from International Application No. PCT/US2013/033716 issued on Oct. 1, 2014.

Aitken & Kirsch "Role of Active-Site Residues Thr81, Ser82, Thr85, Gln157, and Tyr158 in Yeast Cystathionine B-Synthase Catalysis and Reaction Specificity" Biochemistry 43:1963-71 (2004).

Majtan & Kraus "Folding and activity of mutant cystathionine β-synthase depends on the position and nature of the purification tag: characterization of the R266K CBS mutant." Protein Expr Purif. 82(2):317-24 (2012).

* cited by examiner

Figure 1

RC-1-64 DEAE FF (DEAE/IMAC/HIC Process Train)

Date: 04/21/11
Expt No: RC-3-10
Expt No: RC-1-64
Total Protein Mass loaded: 26 mg/mL
30

| Fraction ID | Weight or Volume (g or mL) | CONV. | Protein (mg/mL) | Total Protein in fraction (mg) | Cystathionine from assay (nmol/mL·hr) | Dilution factor from assay | Total Units in fraction | S.A. Fraction | % Rec. Units (%) | % Rec. Total Protein (%) |
|---|---|---|---|---|---|---|---|---|---|---|
| CE Pre-Spin | 37.6 | 1.0 | 20.9 | 784.3 | 46423 | 40 | 69820 | 89.0 | 100.0% | 100.0% |
| Ce Post-Spin | 36.3 | 1.0 | 20.7 | 752.9 | 52427 | 40 | 76124 | 101.1 | 109.0% | 96.0% |
| DEAE Load | 49.8 | 1.0 | 15.4 | 766.8 | 36740 | 40 | 73186 | 95.4 | 96.1% | 101.8% |
| DEAE FT | 49.7 | 1.0 | 3.0 | 151.0 | 3403 | 1 | 169 | 1.1 | 0.2% | 20.1% |
| DEAE Void | 31 | 1.0 | 0.3 | 8.8 | 10298 | 1 | 319 | 36.4 | 0.4% | 1.2% |
| DEAE Eluate | 24.9 | 1.0 | 5.2 | 130.0 | 63422 | 40 | 63168 | 485.8 | 83.0% | 17.3% |
| DEAE Eluate Tail | 18.9 | 1.0 | 1.9 | 35.16 | 69389 | 5 | 6357 | 186.5 | 8.6% | 4.7% |
| DEAE Wash | 89.3 | 1.0 | 1.6 | 143.16 | 5519 | 1 | 493 | 3.4 | 0.6% | 19.0% |
| DEAE 2M NaCl | 76 | 1.0 | 3.2 | 241.44 | 13335 | 5 | 5295 | 21.9 | 7.0% | 32.1% |

Mass Balance Units: 99.8%
Mass Balance Units (from load): 103.8%
Mass Balance Protein: 94.2%
Recovery units (from load): 96.3%

Buffers:
Equilibration: 0.02 M Na3PO4, 0.05 M NaCl, 10% Ethylene Glycol, pH 7.0
Wash: 0.02 M Na3PO4, 0.05 M NaCl, 10% Ethylene Glycol, pH 7.0
Elution: 0.02 M Na3PO4, 0.137 M NaCl, 10% Ethylene Glycol, pH 7.0
Strip: 2 M NaCl
Sanitize: 1.0 M NaOH
Storage: 0.001 M NaOH

| Fraction ID | Weight or Volume (g or mL) | CONV. | Protein (mg/mL) | Total Protein in fraction (mg) | Cystathionine from assay (nmol.mL.hr) | Dilution factor from assay | Total Units in fraction | S.A. Fraction | % Rec. Units (%) | % Rec. Total Protein (%) |
|---|---|---|---|---|---|---|---|---|---|---|
| CE | 16 | 1.0 | 15.3 | 244.1 | 76039 | 20 | 24332 | 100 | 100.0% | 100.0% |
| IMAC Load | 34.7 | 1.0 | 7.6 | 264.7 | 40608 | 20 | 28321 | 107 | 116.4% | 108.5% |
| IMAC FT | 34.3 | 1.0 | 2.3 | 77.9 | 50 | 20 | 34 | 0 | 0.1% | 31.9% |
| IMAC Equil Wash | 32.6 | 1.0 | 2.8 | 91.6 | 4111 | 1 | 134 | 1 | 0.5% | 37.5% |
| IMAC 5mM Imidazole Wash | 34.3 | 1.0 | 0.6 | 19.2 | 9211 | 1 | 316 | 16 | 1.1% | 7.9% |
| IMAC Void | 6.9 | 1.0 | 0.4 | 3.0 | 38313 | 1 | 264 | 89 | 0.9% | 1.2% |
| IMAC Eluate Front | 14 | 1.0 | 0.7 | 9.8 | 77625 | 1 | 1087 | 110 | 3.8% | 4.0% |
| IMAC Eluate | 16.6 | 1.0 | 4.6 | 77.2 | 75941 | 20 | 25212 | 327 | 89.0% | 31.8% |
| IMAC Eluate Tail | 6.7 | 1.0 | 1.4 | 9.3 | 40388 | 5 | 1353 | 145 | 4.8% | 3.8% |
| IMAC 100mM Imidazole | 38 | 1.0 | 0.4 | 16.7 | 29197 | 1 | 1109 | 66 | 3.9% | 6.8% |

| Mass Balance Units (from load) | Mass Balance Protein |
|---|---|
| 104.2% | 115.1% |

Buffers:
| | |
|---|---|
| Charge | 50 mM NiSO4 |
| Equilibration | 0.02 M Na3PO4, 0.4 M NaCl, 0.002 M Imidazole, 0.01% Triton, pH 7.0 |
| Wash | 0.02 M Na3PO4, 0.4 M NaCl, 0.005 M Imidazole, 0.01% Triton, pH 7.0 |
| Elution | 0.02 M Na3PO4, 0.4 M NaCl, 0.050 M Imidazole, 0.01% Triton, pH 7.0 |
| Strip | 100 mM Imidazole |
| Sanitize | 1 M NaOH |
| Storage | 0.001 M NaOH |

| Bradford Assay (Total Protein) | | | | | | | | | | | | |
|---|---|---|---|---|---|---|---|---|---|---|---|---|
| Date: | 4/18/2011 | | | RC1-63 | | | | | | | | |
| | | | | | | | | | | | | |
| Standard Curve: | | | BSA Stock: | 2000 ug/ml | | Samples: | | | | | | |
| | | Well# | ug/mL BSA | BSA (uL) | Water (uL) | | Number of samples (Don't include triplicates): | | | 6 | | |
| | | 1 | 0 | 0 | 40 | | Amount of Bradford Reagent Needed (mL): | | | 15.4 | | |
| | | 2 | 50 | 1 | 39 | | | | | | | |
| | | 3 | 125 | 2.5 | 37.5 | | | | | | | |
| | | 4 | 250 | 5 | 35 | | | | | | | |
| | | 5 | 500 | 10 | 30 | | | | | | | |
| | | 6 | 750 | 15 | 25 | | | | | | | |
| | | 7 | 1000 | 20 | 20 | | | | | | | |
| | | | | | | | | | | | | |
| | For 10uL per standard, run in triplicate | | | | | | | | | | | |
| | 1 | 2 | 3 | 4 | 5 | 6 | 7 | 8 | 9 | 10 | 11 | 12 |
| A | Std 1 | Std 1 | Std 1 | Sample 1 | Sample 1 | Sample 1 | Sample 9 | Sample 9 | Sample 9 | Sample 17 | Sample 17 | Sample 17 |
| B | Std 2 | Std 2 | Std 2 | Sample 2 | Sample 2 | Sample 2 | Sample 10 | Sample 10 | Sample 10 | Sample 18 | Sample 18 | Sample 18 |
| C | Std 3 | Std 3 | Std 3 | Sample 3 | Sample 3 | Sample 3 | Sample 11 | Sample 11 | Sample 11 | Sample 19 | Sample 19 | Sample 19 |
| D | Std 4 | Std 4 | Std 4 | Sample 4 | Sample 4 | Sample 4 | Sample 12 | Sample 12 | Sample 12 | Sample 20 | Sample 20 | Sample 20 |
| E | Std 5 | Std 5 | Std 5 | Sample 5 | Sample 5 | Sample 5 | Sample 13 | Sample 13 | Sample 13 | Sample 21 | Sample 21 | Sample 21 |
| F | Std 6 | Std 6 | Std 6 | Sample 6 | Sample 6 | Sample 6 | Sample 14 | Sample 14 | Sample 14 | Sample 22 | Sample 22 | Sample 22 |
| G | Std 7 | Std 7 | Std 7 | Sample 7 | Sample 7 | Sample 7 | Sample 15 | Sample 15 | Sample 15 | Sample 23 | Sample 23 | Sample 23 |
| H | | | | Sample 8 | Sample 8 | Sample 8 | Sample 16 | Sample 16 | Sample 16 | Sample 24 | Sample 24 | Sample 24 |

1) Remove appropriate amount of reagent and let it come to RT
2) Add 10ul Standard or sample to each well
3) Add 300ul Reagent to each well using multichannel pipettor
4) Incubate at RT 10min
5) Read on VersaMax

| Sample # | | Dilution | Protein (uL) | Water (uL) | Bradford (ug/mL) | ug/uL |
|---|---|---|---|---|---|---|
| 1 | Post Spin CE Load | 100 | 2 | 198 | 32187.2 | 32.187209 |
| 2 | Equil Wash | 20 | 10 | 190 | 11830.2 | 11.930182 |
| 3 | FT | 10 | 20 | 180 | 3310.39 | 3.310385 |
| 4 | 5mM Wash | 10 | 20 | 180 | 252.568 | 0.252568 |
| 5 | 8mM Wash | 10 | 20 | 180 | 670.278 | 0.670278 |
| 6 | 20mM Wash | 10 | 20 | 180 | 524.895 | 0.524895 |

PURIFICATION OF CYSTATHIONINE BETA-SYNTHASE

CROSS-REFERENCE TO RELATED APPLICATIONS

This application is a non-provisional application of U.S. Provisional Application No. 61/615,629, filed Mar. 26, 2012, the disclosure of each of which is incorporated by reference.

FIELD OF THE INVENTION

The present invention generally relates to methods for purification of Cystathionine β-Synthase (CBS), particularly truncated variants thereof. The present invention also relates to compositions of substantially pure CBS produced through said methods of purification.

BACKGROUND OF THE INVENTION

Cystathionine β-synthase (CBS) plays an essential role in homocysteine (Hcy) metabolism in eukaryotes (Mudd et al., 2001, in *The Metabolic and Molecular Bases of Inherited Disease,* 8 Ed., pp. 2007-2056, McGraw-Hill, New York). The CBS enzyme catalyzes a pyridoxal 5'-phosphate (PLP; Vitamin $B_6$)-dependent condensation of serine and homocysteine to form cystathionine, which is then used to produce cysteine by another PLP-dependent enzyme, cystathionine γ-lyase. In mammalian cells that possess the transsulfuration pathway, CBS occupies a key regulatory position between the remethylation of Hcy to methionine or its alternative use in the biosynthesis of cysteine. The relative flux between these two competing pathways is roughly equal and is controlled by intracellular S-adenosylmethionine (AdoMet) concentrations (Finkelstein and Martin, 1984, *J. Biol. Chem.* 259:9508-13). AdoMet activates the mammalian CBS enzyme by as much as 5-fold with an apparent dissociation constant of 15 μM (Finkelstein et al., 1975, *Biochem. Biophys. Res. Commun.* 66: 81-87; Roper et al., 1992, *Arch. Biochem. Biophys.* 298: 514-521; Kozich et al., 1992, *Hum. Mutation* 1: 113-123).

The C-terminal regulatory domain of human CBS consists of ~140 amino acid residues (Kery et al., 1998, *Arch. Biochem. Biophys.* 355: 222-232). This region is required for tetramerization of the human enzyme and AdoMet activation (Kery et al., 1998, id.). The C-terminal regulatory region also encompasses the previously defined "CBS domains" (Bateman, 1997, *Trends Biochem. Sci.* 22: 12-13). These hydrophobic sequences (CBS 1 and CBS 2), spanning amino acid residues 416-468 and 486-543 of SEQ ID NO: 1, respectively, are conserved in a wide range of otherwise unrelated proteins. Their function remains unknown, although the sharp transition of thermally induced CBS activation and the observation that mutations in this domain can constitutively activate the enzyme indicates that they play a role in the autoinhibitory function of the C-terminal region (Janosik et al., 2001, *Biochemistry* 40: 10625-33; Shan et al., 2001, *Hum. Mol. Genet.* 10: 635-643; Miles and Kraus, 2004, *J. Biol. Chem.* 279: 29871-4). Two well-conserved CBS domains are also present in the C-terminal region of the yeast CBS, which is of approximately the same length as the human enzyme.

In healthy normal individuals, CBS-mediated conversion of Hcy to cystathionine is the rate-limiting intermediate step of methionine (Met) metabolism to cysteine (Cys). Vitamin $B_6$ is an essential coenzyme for this process. In patients with certain genetic mutations in the CBS enzyme, the conversion of Hcy to cystathionine is slowed or absent, resulting in elevations in the serum concentrations of the enzymatic substrate (Hcy) and a corresponding decrease in the serum concentrations of the enzymatic product (cystathionine). The clinical condition of an elevated serum level of Hcy, and its concomitant excretion into the urine, is collectively known as homocystinuria.

Deficiency of CBS is the most common cause of inherited homocystinuria, a serious life-threatening disease that results in severely elevated homocysteine levels in plasma, tissues and urine. Estimates on the prevalence of homocystinuria vary widely. Ascertainment by newborn screening and clinical ascertainment have indicated a prevalence ranging from 1:200,000 to 1:335,000 (Mudd et al., 1995, *The Metabolic and Molecular Basis of Inherited Diseases*, McGraw-Hill: New York, p. 1279). The primary health problems associated with CBS-deficient homocystinuria (CBSDH) include: cardiovascular disease with a predisposition to thrombosis, resulting in a high rate of mortality in untreated and partially treated patients; connective tissue problems affecting the ocular system with progressive myopia and lens dislocation; connective tissue problems affecting the skeleton characterized by marfanoid habitus, osteoporosis, and scoliosis; and central nervous system problems, including mental retardation and seizures. Symptoms include dislocated optic lenses, skeletal disorders, mental retardation and premature arteriosclerosis and thrombosis (Mudd et al., 2001, id.). Homozygous CBS deficiency is associated with a multitude of clinical symptoms, including mental retardation, osteoporosis, kyphoscoliosis, stroke, myocardial infarction, ectopia lentis, and pulmonary embolism. Cardiovascular complications of the disease, in particular arterial and venous thrombosis, are the principal contributors to early mortality.

The pathophysiology of CBS deficiency is undoubtedly complex, but there is a consensus that the fundamental instigator of end-organ injury is an extreme elevation of serum Hcy, a substrate of CBS that builds-up in tissues and blood due to the absence of its CBS-catalyzed condensation with L-serine to form cystathionine. The toxicity of profound elevations in blood and tissue concentrations of Hcy may ensue from the molecular reactivity and biological effects of Hcy per se or from its metabolites (e.g. Hcy-thiolactone) that affect a number of biological processes (Jakubowski et al., 2008, *FASEB J* 22: 4071-6). Abnormalities in chronic platelet aggregation, changes in vascular parameters, and endothelial dysfunction have all been described in patients with homocystinuria.

Currently, three treatment options exist for the treatment of CBSDH:
1) Increase of residual activity of CBS activity using pharmacologic doses of Vitamin $B_6$ in Vitamin $B_6$-responsive patients
2) Lowering of serum Hcy by a diet with a strict restriction of the intake of Met; and
3) Detoxification by betaine-mediated conversion of Hcy into Met, thus lowering serum Hcy concentration.

Each of these three therapies is aimed at lowering serum Hcy concentration. The standard treatment for individuals affected with Vitamin $B_6$ non-responsive CBSDH consists of a Met-restricted diet supplemented with a metabolic formula and Cys in the form of cysteine (which has become a conditionally essential amino acid in this condition). Intake of meat, dairy products, and other food high in natural protein is prohibited. Daily consumption of a poorly palatable, synthetic metabolic formula containing amino acids and micronutrients is required to prevent secondary malnutrition. Supplementation with betaine (trade name: Cystadane™, synonym: trimethylglycine) is also standard therapy, wherein betaine serves as a methyl donor for the remethylation of Hcy to Met catalyzed by betaine-homocysteine methyltransferase in the liver (Wilcken et al., 1983, *N. Engl. J. Med.* 309: 448-53). Dietary compliance generally has been poor, even in those medical centers where optimal care and resources are provided, and this non-compliance has major implications on the development of life-threatening complications of homocystinuria.

To enable patients with homocystinuria enjoy a far less restrictive diet (e.g. daily intake limited to 2 g protein per kg, which is easily attainable), and have a significantly decreased Hcy plasma level leading in the long-term to clinical improvement, a strategy for increasing enzyme activity provides potential for treatment as set forth in co-pending U.S. provisional patent application Ser. No. 61/758,138. The most effective therapeutic strategy is to increase enzyme activity, as is evident when Vitamin $B_6$-responsive homocystinuria patients are given pyridoxone. However, this strategy is not possible for Vitamin $B_6$ non-responsive patients due to the nature of the mutations. Enzyme replacement therapy (ERT) as a way to increase enzyme activity in these patients requires exogenous enzyme, which is not present in the art and thus raises a need in the art for improved reagents and methods for producing CBS in greater yields of sufficiently purified enzyme for therapeutic administration.

Kraus and colleagues have developed expression systems and fermentation conditions for generating active recombinant human CBS and variants thereof (U.S. Pat. Nos. 5,635,375, 5,523,225 and 7,485,307, incorporated by reference herein in their entireties for any purpose). These proteins were purified by processes relevant for academic purposes, including use of protein leads on the proteins which are not considered useful for preparation of pharmaceuticals.

In order to employ methods of increasing CBS enzyme activity, an efficient method of CBS enzyme purification is required. Existing methods of purification for recombinant CBS protein rely on affinity tags to facilitate purification that does not provide the desired purity and efficiency. Therefore to more efficiently obtain the necessary levels of CBS required for therapeutic use there is a need for improved downstream purification of CBS protein produced in microbial cells.

SUMMARY OF THE INVENTION

This invention provides methods for purifying cystathionine β-Synthase (CBS), wherein said CBS protein is a naturally occurring truncated variant, or a chemically cleaved or genetically engineered truncate thereof, and particularly truncated CBS produced in recombinant cells. In particular embodiments, the method comprises the steps of: (a) providing a CBS-containing solution in the presence of at least one impurity; and (b) performing chromatographic separation of said CBS-containing solution using a metal affinity chromatography (IMAC) resin. In additional particular embodiments, the method comprises the steps of: (a) providing a CBS-containing solution in the presence of at least one impurity; and (b) performing chromatographic separation of said CBS-containing solution using an ion exchange chromatography column and a metal affinity chromatography (IMAC) resin.

In certain embodiments the method further comprises performance of additional chromatographic steps (known in the art as "polishing" steps). In particular embodiments, the methods of the invention include the step of performing chromatographic separation using a Hydrophobic Interaction Chromatography (HIC) column. In other embodiments the method further comprises the step of performing chromatographic separation using a ceramic hydroxyapaptite resin.

In certain embodiments the ion exchange column is an anion exchanger, preferably a weak anion exchanger. In particular embodiments the anion exchanger is a DEAE-Sepharose FF column. In further embodiments the IMAC resin is charged with a divalent ion. In yet further embodiments the divalent metal ion is nickel, copper, cobalt or zinc. In more specific embodiments the divalent metal ion is zinc.

In certain other embodiments the method further comprises eluting CBS from the IMAC resin with an elution buffer comprising imidazole. In certain embodiments the CBS-containing solution is a clarified CBS solution, wherein cell debris and other particulate matter is removed from a suspension comprising CBS including but not limited to supernatant after centrifugation or filtrate after filtration. In yet other embodiments the CBS-containing solution is obtained by homogenizing cells expressing a recombinant construct comprising a nucleic acid sequence encoding CBS. In certain embodiments the CBS nucleic acid sequence comprises SEQ ID NO. 1 and encodes a protein have the amino acid sequence identified as SEQ ID NO: 2. In other embodiments the nucleic acid sequence is truncated. In yet other embodiments the truncated CBS nucleic acid sequence has been truncated to an ending position of one of amino acid residues from 382-532, 382-550 or 543-550 of SEQ ID NO:2

In other certain embodiments the recombinant cells are microbial cells, particularly bacterial cells. In particular embodiments, the bacterial cells are *E. coli* cells, particularly recombinant *E. coli* cells that produce a mammalian, preferably human, CBS protein. In certain particular embodiments, said human CBS protein has an amino acid sequence as set forth in SEQ ID NO:3 or a truncated CBS nucleic acid sequence that has been truncated to an ending position of one of amino acid residues from 382-532 or 543-550 of SEQ ID NO:2. In other particular embodiments, the truncated CBS nucleic acid sequence is optimized for expression in *E. coli*, identified by SEQ ID NO: 4.

In another aspect, a substantially purified CBS solution is provided using a method comprising the steps of: a) providing a CBS-containing solution in the presence of at least one impurity, wherein said CBS protein is a naturally occurring truncated variant, or a chemically cleaved or genetically engineered truncate thereof, and particularly truncated; and (b) performing chromatographic separation of said CBS-containing solution using a metal affinity chromatography (IMAC) resin. In additional particular embodiments, a substantially purified CBS solution is provided using a method comprising the steps of: (a) providing a CBS-containing solution in the presence of at least one impurity; and (b) performing chromatographic separation of said CBS-containing solution using an ion exchange chromatography column and a metal affinity chromatography (IMAC) resin.

In certain embodiments of the invention the substantially purified CBS solution is formulated in a pharmaceutically acceptable carrier.

In another aspect, the invention provides methods for producing an enriched CBS solution, the method comprising of: (a) providing a CBS-containing solution in the presence of at least one impurity, wherein said CBS protein is a naturally occurring truncated variant, or a chemically cleaved or genetically engineered truncate thereof, and particularly truncated; and (b) performing chromatographic separation of said CBS-containing solution using an immobilized metal affinity chromatography (IMAC) resin charged with a divalent metal ion.

In another aspect, an enriched CBS solution is provided using a method comprising the steps of: a) providing a CBS-containing solution in the presence of at least one impurity, wherein said CBS protein is a naturally occurring truncated variant, or a chemically cleaved or genetically engineered truncate thereof, and particularly truncated; and (b) performing chromatographic separation of said CBS-containing solution using an immobilized metal affinity chromatography (IMAC) resin charged with a divalent metal ion.

It is a particular advantage of this invention that purification of recombinant, full-length or truncated CBS, particularly human CBS, can be achieved without further modification of the protein, e.g., by incorporating a "tag" molecule known in the art (poly-HIS, FLAG, etc.). Use of the chromatographic methods disclosed herein advantageously makes these tags unnecessary, thus avoiding additional recombinant manipulation and any disadvantages (in immunogenicity, in vivo half-life or biochemical activity) that might be introduced into any preparation of recombinant CBS containing such a tag.

Specific preferred embodiments of the invention will become evident from the following more detailed description of certain preferred embodiments and the claims.

BRIEF DESCRIPTION OF DRAWINGS

The following detailed description of the embodiments of the present invention can be best understood when read in conjunction with the following drawings.

FIG. 1 is a purification train summary from scale-up generation runs using a multi-step chromatography method including DEAE-Sepharose-FF, Zn-IMAC and HIC chromatography.

FIG. 2 is a purification summary from purification experiments using a DEAE-Sepharose-FF column and CBS purified using the "non-optimized" bacterial expression construct. Mobile phases included 10% ethylene glycol in addition to other components as set forth in the Examples.

FIG. 3 is a purification train summary from scale-up generation runs using a multi-step chromatography method including DEAE-Sepharose-FF, Zn-IMAC, ceramic hydroxyapaptite resin and HIC chromatography.

FIG. 8 is a purification summary from development runs using a Ni-IMAC column.

FIG. 9 is a summary table demonstrating the total protein following a purification method using a Ni-IMAC column.

FIG. 11 is a purification summary from scale-up generation runs using a Cu-IMAC column.

FIG. 12 is a summary table demonstrating the total protein following a purification method using a Zn-IMAC column.

DETAILED DESCRIPTION OF THE INVENTION

Figure 4:
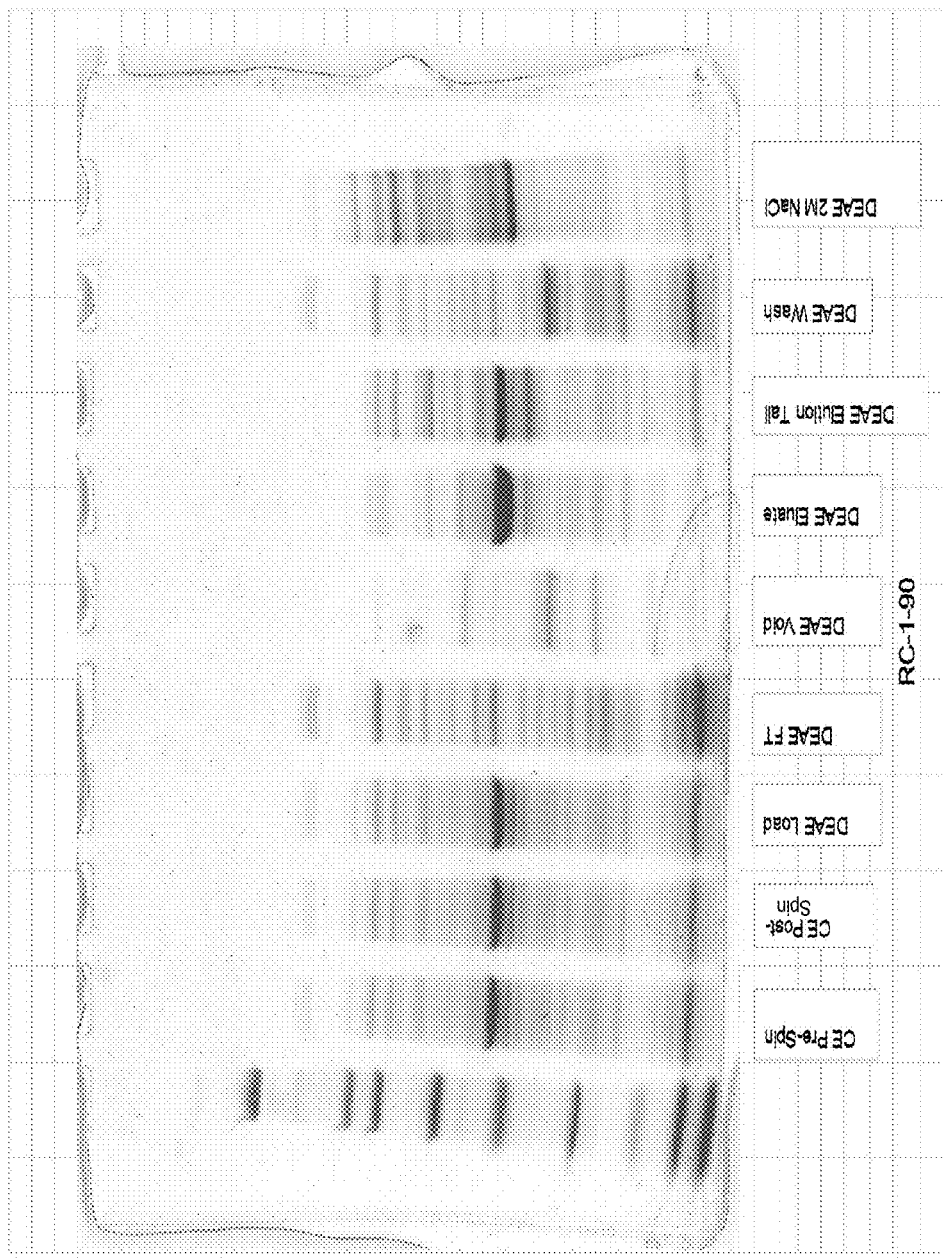
FIG. 4 is a photoimage of a SDS page gel showing the relative amounts of CBS protein and impurities for each stage of the purification step using a DEAE column.

This invention provides methods for purification of CBS protein, wherein said CBS protein is a naturally occurring truncated variant, or a chemically cleaved or genetically engineered truncate thereof, and particularly a truncated protein CBS produced in recombinant cells. In particular, the invention provides methods for the purification of a CBS protein that include the steps (a) providing a CBS-containing solution in the presence of at least one impurity; and (b) performing chromatographic separation of said CBS-containing solution using a metal affinity chromatography (IMAC) resin. In additional particular embodiments, the method comprises the steps of: (a) providing a CBS-containing solution in the presence of at least one impurity; and (b) performing chromatographic separation of said CBS-containing solution using an ion exchange chromatography column and a metal affinity chromatography (IMAC) resin.

A particular chromatographic separation step in the certain embodiments of the methods provided by this invention comprises an ion exchange chromatography column. In one embodiment, the ion exchange chromatography column is an anion exchanger, preferably a weak anion exchanger. Various types of anion exchange resins can be used, including DEAE-Sephadex, QAE-Sephadex, DEAE-Sephacel, DEAE-cellulose and DEAE-Sepharose-FF. According to one embodiment, the anion exchange resin is DEAE-Sepharose-FF.

Another particular chromatographic separation step in the certain of the methods provided by this invention comprises a metal affinity chromatography (IMAC) resin having appropriate pH and conductivity such to allow the protein to bind to the column while selective intermediate washes are used to remove weaker binding proteins and other molecular species. In certain embodiments, varying concentrations of imidazole were used to modulate the partitioning during the chromatography. Suitable metal affinity resins include immobilized metal affinity columns charged with a divalent metal ion including nickel, copper, cobalt or zinc. In certain embodiments of the methods of the invention, the metal affinity chromatography (IMAC) column is used following ion exchange chromatography. In such embodiments, the IMAC column is preferably charge with zinc as a divalent cation. In other embodiments of the inventive methods, the IMAC column is used as an initial chromatographic step. In such embodiments, nickel or copper divalent cations are preferably used to charge the IMAC column.

Additional chromatographic steps provided in certain embodiments of the methods of this invention for purifying CBS from a CBS-containing solution include without limitation hydrophobic interaction chromatography (HIC). HIC is useful for removing impurities that have relatively closely related chromatographic properties that are eluted together with the target protein during the capture step.

Further additional chromatographic steps provided in certain embodiments of the methods of this invention for purifying CBS from a CBS-containing solution include without limitation a ceramic hydroxyapatite resin. "Ceramic hydroxyapatite" or "CHAP" refers to an insoluble hydroxylated calcium phosphate of the formula $(Ca_{10}(PO_4)_6(OH)_2)$, which has been sintered at high temperatures into a spherical, macroporous ceramic form. The methods of the invention also can be used with hydroxyapatite resin that is loose or packed in a column. The choice of column dimensions can be determined by the skilled artisan.

Chromatography matrices useful in the method of the invention are materials capable of binding biochemical compounds, preferably proteins, nucleic acids, and/or endotoxins, wherein the affinity of said biochemical compounds to said chromatography matrix is influenced by the ion composition of the surrounding solution (buffer). Controlling the ion composition of said solution allows to use the chromatography materials of the invention either in subtractive mode (CBS passes through said chromatography matrix, at least certain contaminants bind to said chromatography matrix) or, preferably, in adsorptive mode (CBS binds to the chromatography matrix).

In particular embodiments, the method for purification comprises the step of homogenizing host cells, particularly recombinant cells and in certain embodiments, recombinant cells producing mammalian, preferable human, CBS protein, wherein said recombinant construct encodes a CBS protein that is a naturally occurring truncated variant, or a genetically engineered truncate thereof, and particularly wherein said construct has been optimized for recombinant cell expression. In particular embodiments, said recombinant cells are microbial cells and particularly bacterial cells. In certain particular embodiments, the bacterial cells are *E. coli* cells and the CBS sequence has been engineered in the recombinant expression construct to be optimized for expression in said cells; a specific embodiment of such a nucleic acid sequence optimized for CBS expression in *E. coli* is set forth in SEQ ID NO: 4. In said methods, cells are harvested, e.g. by centrifugation, and optionally stored at −80 degree ° C. Homogenization of host cells is performed by disrupting the cells host using physical, chemical or enzymatic means or by a combination thereof. Advantageously, for purification from bacterial sources homogenation is performed by disrupting the cell wall of said bacterial host by sonication. Alternatively or additionally homogenizing is performed by destabilizing the bacterial cell wall of the host by exposure to a cell wall degrading enzyme such as lysozyme.

The methods of the invention can further comprise a clarified CBS homogenate, wherein cell debris is removed from the homogenate by either filtration or centrifugation. In certain embodiments, clarifying is performed by centrifuging the homogenate at an effective rotational speed. The required centrifugation time depends inter alia on the volume of the homogenate, which can be determined empirically to obtain a sufficiently solid pellet. To obtain an essentially cell debris-free clarified homogenate a combination of centrifugation and filtration can be performed on the homogenate.

The term "recombinant cell" as used herein refers to suitable cells (including progeny of such cells) from any species into which has been introduced a recombinant expression construct capable of expressing a nucleic acid encoding CBS protein, preferably human CBS protein and most particularly a human CBS protein that is a naturally occurring truncated variant, or a chemically cleaved or genetically engineered truncate thereof. In specific embodiments, the truncated CBS protein encoded by said recombinant expression construct has an amino acid sequence as set forth in SEQ ID NO: 3.

The term, "bacterial cell", as used herein refers to bacteria that produces a mammalian, preferably human, CBS protein inter alia using recombinant genetic methods including progeny of said recombinant cell, wherein said CBS protein is a naturally occurring truncated variant, or a genetically engineered truncate thereof.

The term "recombinant expression construct" as used herein refers to a nucleic acid having a nucleotide sequence of a mammalian, preferably human, CBS protein, and sequences sufficient to direct the synthesis of CBS protein in cultures of cells into which the recombinant expression construct is introduced and the progeny thereof.

As used herein, reference to CBS protein or polypeptide preferably includes a naturally occurring truncated variant, or a chemically cleaved or genetically engineered truncate thereof, or fusion proteins, or any homologue (variant, mutant) thereof, and specifically mammalian CBS and preferably human CBS. Such a CBS protein can include, but is not limited to, purified CBS protein, recombinantly produced CBS protein, soluble CBS protein, insoluble CBS protein, and isolated CBS protein associated with other proteins. In addition, a "human CBS protein" refers to a CBS protein from a human (*Homo sapiens*) preferably includes a naturally occurring truncated variant, or a chemically cleaved or genetically engineered truncate thereof. As such, a human CBS protein can include purified, partially purified, recombinant, mutated/modified and synthetic proteins. As disclosed herein and in related U.S. Pat. Nos. 8,007,787 and 7,485,307, the CBS protein truncates are advantageously soluble CBS proteins that are produced in bacteria without the creation of insoluble inclusion bodies.

As used herein, the term "homologue" (or variant or mutant) is used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form. Such changes include, but are not limited to: changes in one, few, or even several amino acid side chains; changes in one, few or several amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, changed, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis. CBS variants are described in U.S. Pat. No. 8,007,787, which is incorporated herein by reference in its entirety; in particular and preferred embodiments, the reagents and methods of the invention set forth herein preferably include a naturally occurring truncated variant, or a chemically cleaved or genetically engineered truncate of human CBS protein. Particular truncated forms of SEQ ID NO: 3 according to the present invention include N-terminal deletion variants, C-terminal deletion variants, and variants having both N-terminal and C-terminal deletions.

As used herein, "substantially pure" refers to a purity that allows for the effective use of the protein in vitro, ex vivo or in vivo. For a protein to be useful in vitro, ex vivo or in vivo, it is preferably substantially free of contaminants, other proteins and/or chemicals that might interfere or that would interfere with its use, or that at least would be undesirable for inclusion with a CBS protein (including homologues thereof).

As used herein an enriched CBS solution is a solution subjected to one or more purification steps.

The purity of protein can be determined by calculating fold purification, i.e. a formula that provides a measure of how much more a purified solution is compared to a less purified solution or crude extract. Fold purification is calculated using the following formula:

Specific activity final fraction/Specific activity crude fraction.

Another measurement to assess purity is the "specific activity" which measures the purity of an enzyme. Specific activity can be measured using the following formula:

$$\frac{\text{Units}}{\text{mL}} \times \frac{\text{mL}}{\text{mg}} = \frac{\text{Units}}{\text{mg}}$$

CBS protein compositions provided by this invention are useful for regulating biological processes and particularly, processes associated with the catalysis of the pyridoxal 5'-phosphate (PLP)-dependent condensation of serine and homocysteine to form cystathionine. In particular, compositions of the present invention are useful for producing cystathionine and cysteine in vitro or for treating a patient that will benefit from increased CBS activity (e.g., a patient with homocystinuria). In certain embodiments, the invention provides said compositions of CBS protein, preferably human CBS protein, wherein said CBS protein is a naturally occurring truncated variant, or a chemically cleaved or genetically engineered truncate of human CBS protein, as pharmaceutical compositions comprising said CBS protein and a pharmaceutically acceptable carrier.

As used herein, a "pharmaceutically acceptable carrier" includes pharmaceutically acceptable excipients and/or pharmaceutically acceptable delivery vehicles, suitable for use in suitable administration of the composition in vitro, ex vivo or in vivo. Suitable in vitro, in vivo or ex vivo administration preferably comprises any site where it is desirable to regulate CBS activity. Suitable pharmaceutically acceptable carriers are capable of maintaining a CBS protein as provided by this invention in a form that, upon arrival of the protein at the target cell or tissue in a culture or in patient, the protein has its expected or desired biological activity. Examples of pharmaceutically acceptable carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

Each reference described and/or cited herein is incorporated by reference in its entirety.

The following examples are provided for the purpose of illustration and are not intended to limit the scope of the present invention.

EXAMPLES

Example 1

Production of Truncated CBS Protein in Bacteria

A truncated human CBS variant lacking specific portions of the non-conserved regions (r-hCβSΔC; SEQ ID No: 3) were constructed and over-expressed using the previously described *E. coli* based expression system (Kozich and Kraus, 1992, supra). In the modification of this system disclosed herein (i.e., expressing the truncate rather than the full-length CBS protein), the CBS truncate encoded by SEQ ID NO: 3 was expressed without any fusion partner under the control of the tac promoter. Constructs encoding the truncated human CBS protein variant r-hCβSΔC (SEQ ID NO: 4) were generated by a modification of the previously described pHCS3 CBS expression construct (Kozich and Kraus, 1992, Hum. Mutat. 1, 113-123) which contains the CBS full-length coding sequence (SEQ ID NO: 1) cloned into pKK388.1. In this construct, CBS expression was governed by the IPTG inducible lac promoter. To generate C-terminal deletion constructs, CBS cDNA fragments spanning the desired nucleotide residues were amplified using primers incorporating Sph I and Kpn I sites to the 5' and 3' respective ends of the PCR product. All PCR products were then cut with Sph I and Kpn I and cloned by ligation into the pHCS3 vector digested with Sph I and Kpn I. An Sph I site naturally occurs in the CBS cDNA, just upstream of the antisense primer hybridization site (base pare position 1012, according to the CBS cDNA numbering, ref. 25). PCR products thus generated were then digested with Nco I and Sph I and ligated into the pHCS3 plasmid cut with the same enzymes.

pKK CBS Δ414-551
sense:
                                                    (SEQ ID NO: 5)
CGTAGAATTCACCTTTGCCC<u>GCATGC</u>TGAT (SphI)

antisense:
                                                    (SEQ ID NO: 6)
TACG<u>GGTACC</u>TCAACGGAGGTGCCACCACCAGGGC (KpnI)

Finally, the construct was transformed into *E. coli* BL21 (Stratagene). The authenticity of the construct was verified by DNA sequencing using a Thermo Sequenase Cy5.5 sequencing kit (Amersham Pharmacia Biotech) and the Visible Genetics Long-Read Tower System-V3.1 DNA sequencer according to the manufacturer's instructions.

Bacterial Expression Analysis of CBS Deletion Mutants—Growth of *E. coli*.

BL21 cells bearing the CBS truncation mutant construct, induction of expression and the generation of crude cell lysates were performed as described previously (Maclean et al., 2002, *Hum. Mutat.* 19(6), 641-55). Briefly, bacteria were grown at 37° C. aerobically in 1 L NZCYMT media (Gibco/BRL, Gaithersburg, Md.) containing 75 µg/mL ampicilin and 0.001% thiamine in the presence or absence of 0.3 mM δ-aminolevulinate (δ-ALA) until they reached turbidity of 0.5 at 600 nm. IPTG was then added to 0.5 mM and the bacteria were grown further. The insoluble fraction was prepared as follows: after the centrifugation of the sonicated homogenate, pelleted cell debris were thoroughly washed with chilled 1x Tris-buffered saline, pH 8.0. The pellets were then resuspended in 1 ml of the lysis buffer (Maclean et al., ibid.) followed by a brief sonication in order to homogenize the insoluble fraction.

CBS Activity Assay—

CBS activity was determined by a previously described radioisotope assay using [$^{14}$C] serine as the labeled substrate (Kraus, 1987, *Methods Enzymol.* 143, 388-394). Protein concentrations were determined by the Lowry procedure (Lowry et al., 1951, *J. Biol. Chem.* 193, 265-275) using bovine serum albumin (BSA) as a standard. One unit of activity is defined as the amount of CBS that catalyzes the formation of 1 μmol of cystathionine in 1 h at 37° C.

Denaturing and Native Polyacrylamide Gel Electrophoresis and Western Blotting—

Western blot analysis of crude cell lysates under both denaturing and native conditions was performed as described previously (Janosik, 2001, supra) with some modifications. Soluble fractions of *E. coli* lysates containing the expressed mutant protein were mixed with sample buffer and run on a 6% native PAGE without a stacking gel. The final composition of the sample buffer was: 50 mM Tris-HCl, pH 8.9, 1 mM DTT, 10% glycerol, 0.001% bromphenol blue. Detection of heme was performed using a previously described method that relies on heme peroxidase activity (Vargas et al., 1993, *Anal. Biochem.* 209(2), 323-6).

Densitometric Scanning Analysis—

Quantitative densitometry analysis was performed using the Imagemaster ID (version 2.0) software (Pharmacia). To construct a calibration curve, 50, 75, 100, 250, 500 and 1000 ng of purified wild type CBS protein were run on an SDS-PAGE together with crude cell lysates of the individual mutants. Following electrophoresis, Western blot immunoanalysis was conducted using rabbit anti-CBS serum. The signals corresponding to the experimentally observed CBS mutant subunits were all within the linear range of the calibration curve constructed with purified human CBS.

Example 2

Preparation of Crude Extraction

Crude CBS protein-containing extracts was prepared for use in downstream chromatography steps. Frozen pellets (cells) obtained from fermentation of recombinant bacteria producing human truncated CBS variant (r-hCβSΔC; SEQ ID No: 3) were lysed, wherein said bacteria expressed truncated human CBS encoded by SEQ ID NO: 4. Lysis buffer for initial isolations contained 1 mM DTT, 1% Triton X-100, and Protease Inhibitor. These components were eventually removed from the buffer. The buffer used for the final isolations that produced material for scale-up runs consisted of 20 mM Sodium Phosphate, 50 mM NaCl, 0.1 mM PLP (pH 7.2), with lysozyme added to a concentration of 2 mg/mL after homogenization. Following mixing with lysozyme for 1 hr at 4° C., the homogenate was sonicated until viscosity was reduced and then subjected to centrifugation at 20,000 rpm (48,000×g) for 30 min. The supernatant was collected, aliquoted, and stored at −70° C. until use. Generally, the crude extract was thawed at 37° C. prior to chromatographic purification.

Example 3

DEAE-Sepharose FF Chromatography

Figure 1:
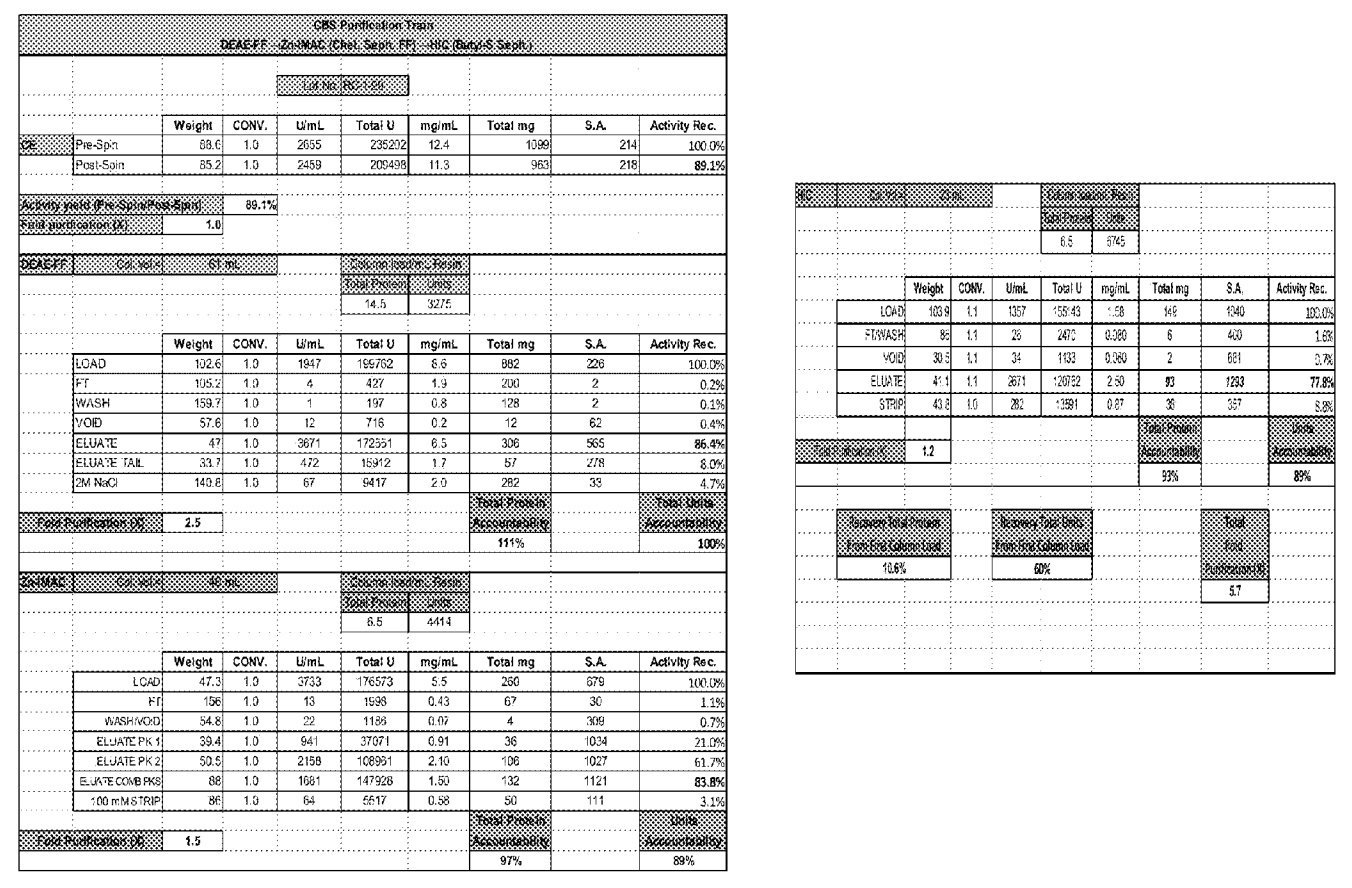
Figure 3:
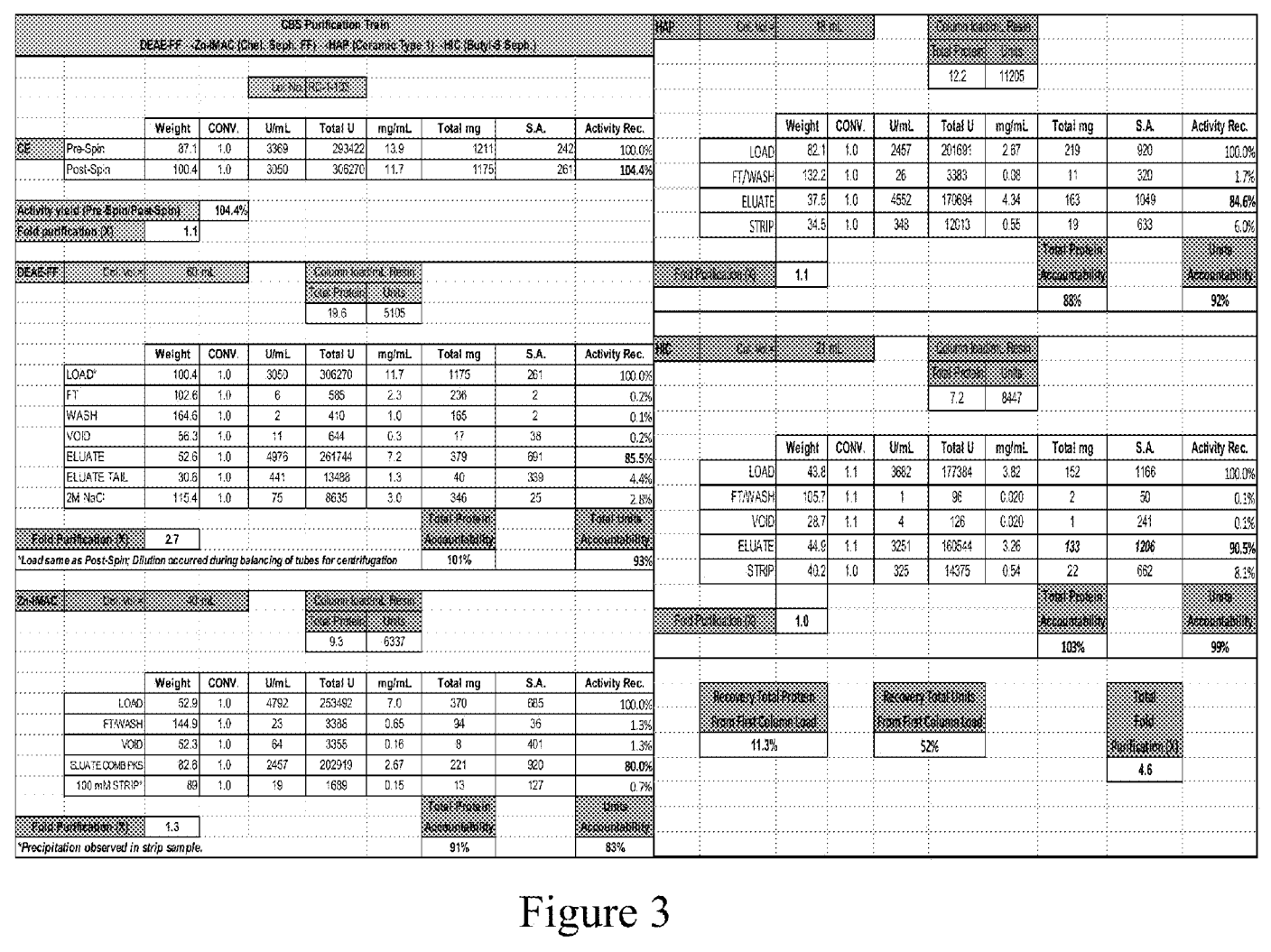

DEAE-Sepharose FF was used in this Example of the purification methods for CBS because it possesses good capacity and flow properties and has been manufactured consistently for several years. This step employed a drip/gravity column that contained approximately 6 mL of resin. The column was equilibrated in Sodium Phosphate buffer with 50 mM NaCl, pH 7.0. Loading of the crude extract was targeted at approximately 20 mg total protein/mL resin. After loading the column, the red color of the load was concentrated near the top of the column. Following a wash with equilibration buffer, the column was washed with a buffer containing 150 mm NaCl, whereby the majority of color eluted from the column (all steps were performed at pH 7.0). Essentially all color was removed from the column with a 300 mM NaCl wash. Based on these results, a column was packed that could be operated in flow mode. The conditions employed equilibration/loading at a NaCl concentration 50 mM, with elution at 250 mM NaCl. The final conditions required dilution of the column load with $H_2O$ to approach the ionic strength of the equilibration/wash buffer (50 mM NaCl), and elution with 137 mM NaCl (FIGS. 1, 2 and 3). Samples were analyzed by SDS-PAGE to determine the relative amounts of CBS protein and impurities (FIG. 4). The following tables represent column operational parameters and data from the scale-up runs that employed them.

TABLE 1

Operational Parameters for DEAE Capture Step

| Process Step | Column load target (total protein mg/mL) | NaCl Concentration (with 20 mM $Na_3PO_4$ pH 7.0) | Column Volumes (mL) | Contact time Column vol./flow rate (min.) |
|---|---|---|---|---|
| Equilibration | N/A | 50 mM | 3-5 | 10 |
| Load | 20-25 mg/mL | Approx. 50 mM | Variable | 15 |
| Wash | N/A | 50 mM | 3 | 10 |
| Elution | N/A | 137 mM | Variable* | 15 |
| 2M NaCl Strip | N/A | 2M | 3 | 10 |

*Note: Eluate collection starts at approx. 0.4 AU and ends at approx. 0.55 AU. Void volume typically approx. 1 column volume.

TABLE 2

Data from Scale-up Runs (n = 6)

| Input Column loading (per mL Resin) | | Output | | |
|---|---|---|---|---|
| Total Protein (mg) | Units | Recovery (%) | Fold Purif. (By S.A.) | |
| 14.5-19.8 | 3275-5443 | 79.3-93.0 | 2.5-3.3 | Range |
| 18.2 | 4451 | 86 | 2.8 | Average |

Example 4

IMAC Chromatography

The ability for an immobilized metal affinity column (IMAC) to separate CBS protein from impurities and other contaminants from a biological source, such as a recombinant bacterial cell homogenate, was demonstrated. Because of the desire to avoid low pH conditions (<5, anecdotal), varying concentrations of imidazole were used to modulate partitioning during the chromatography.

Figure 9:
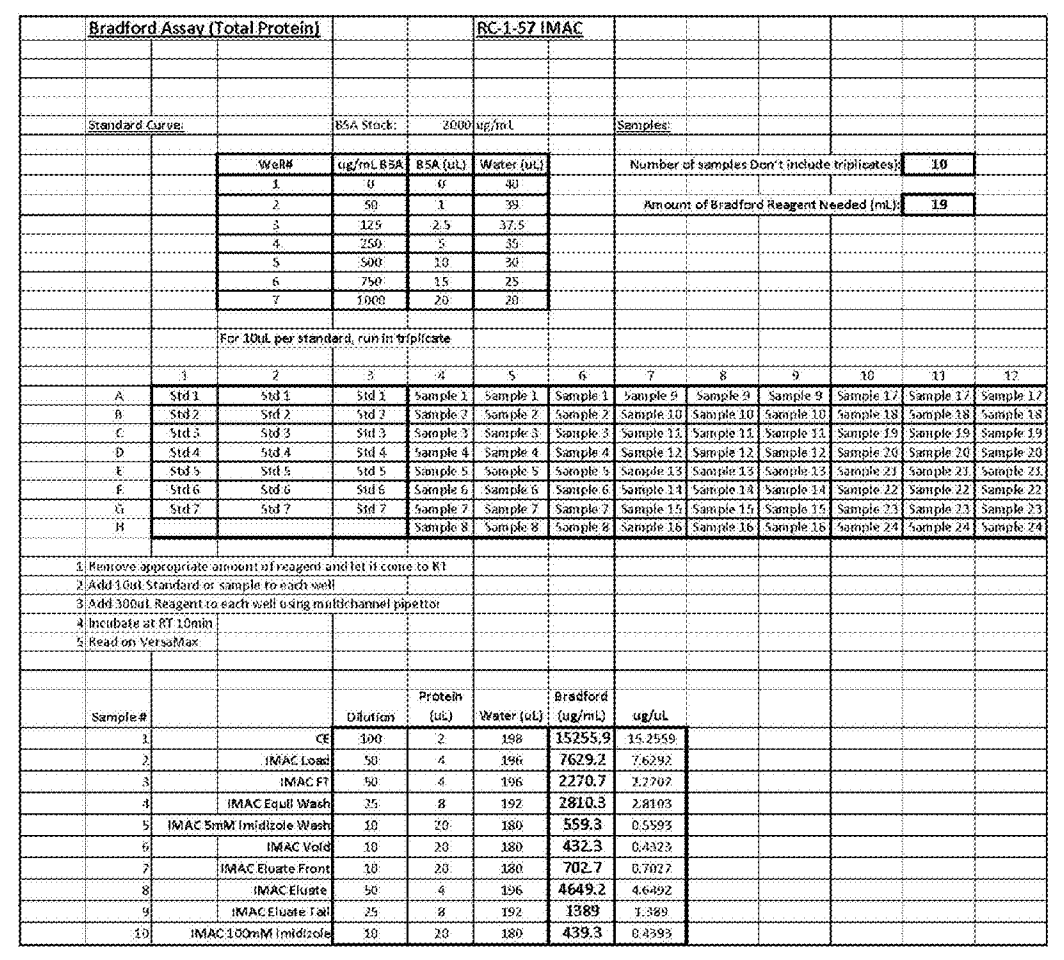
Figure 10:
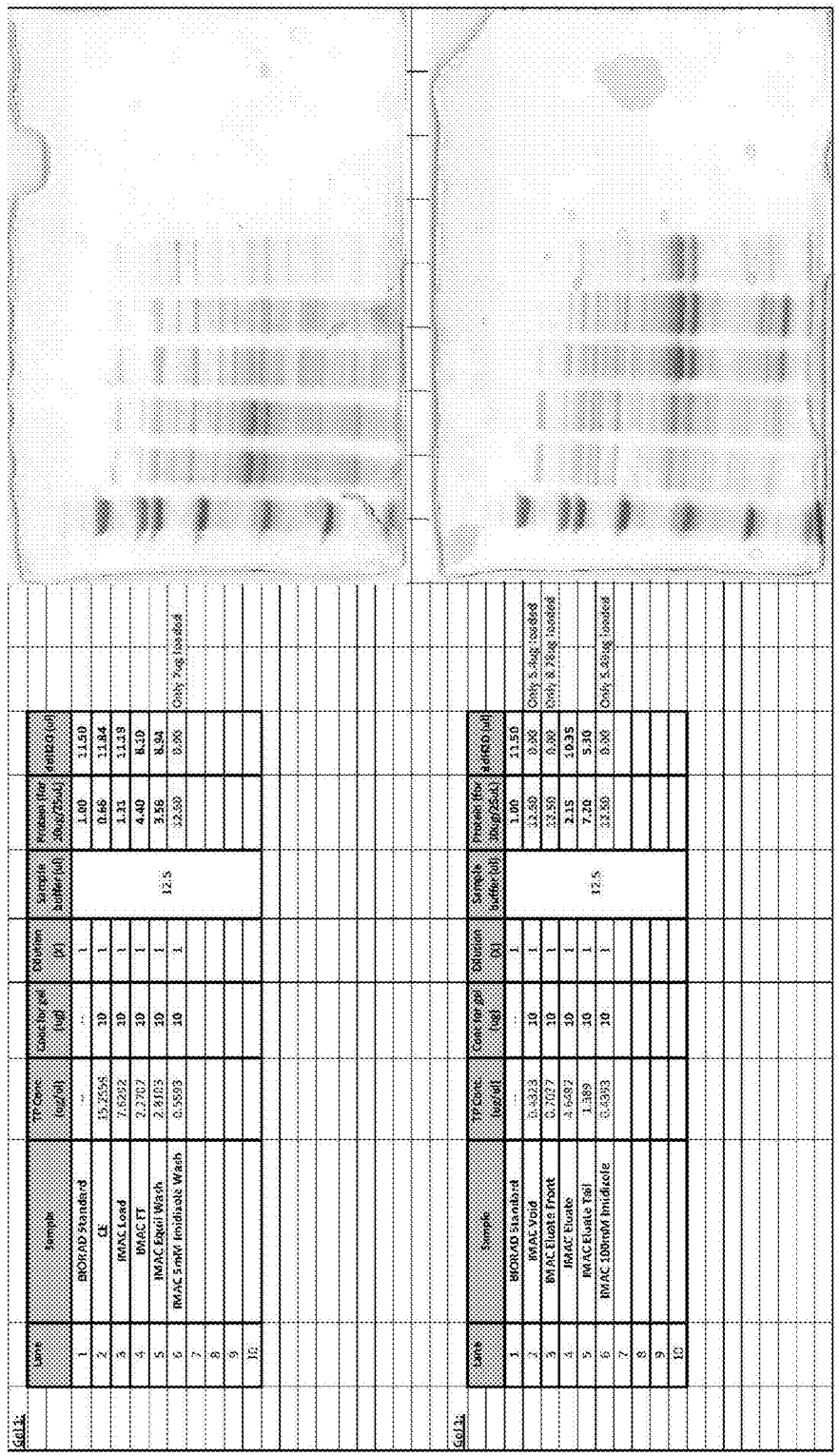
FIG. 10 is a photoimage of a SDS page gel showing the relative amounts of CBS protein and impurities for each stage of the purification step using a Ni-IMAC column.
Figure 11:
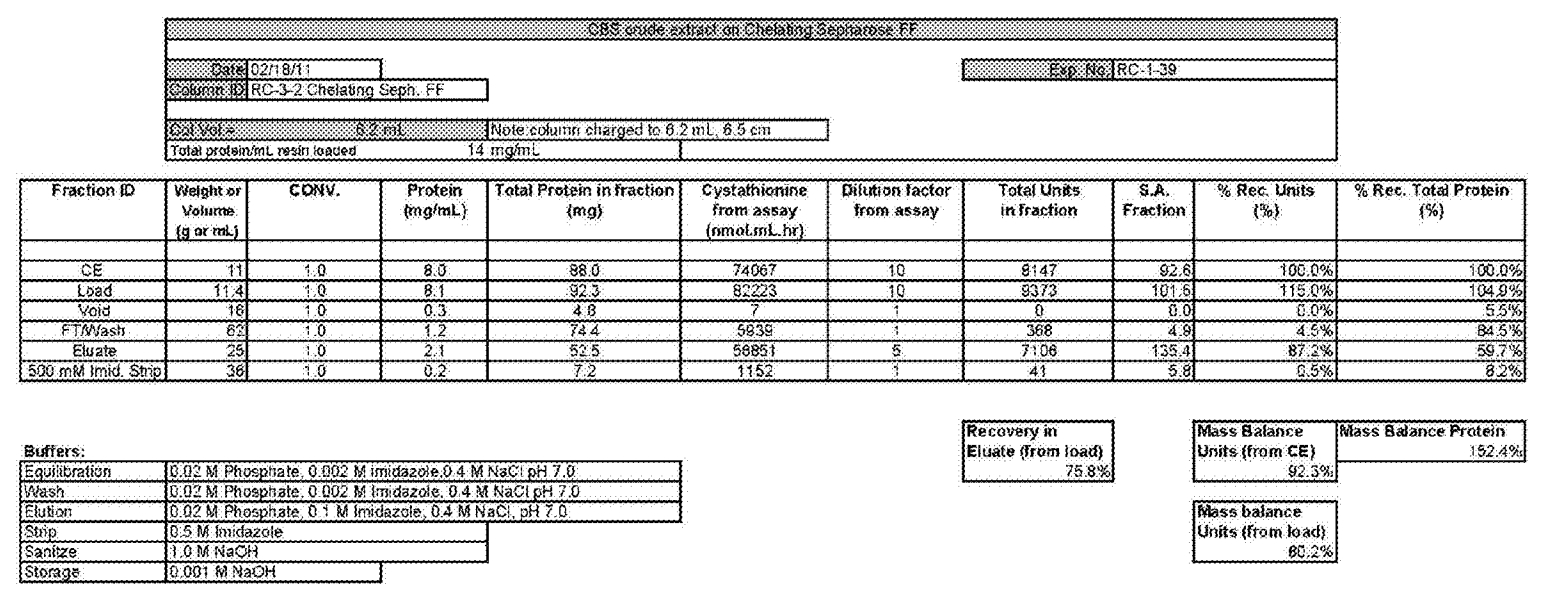

Copper ($Cu^{++}$) was tested as a candidate species of IMAC column based on its relatively strong binding characteristics. Prior to being applied to the IMAC column, the CBS solution was adjusted to 0.4M NaCl. The results indicated that capture was near complete, with an acceptable activity recovery (70-80%). Recovery of CBS was obtained using 100 mM imidazole, which resulted in significant precipitation upon thawing from storage at −70° C. (FIG. 11). In addition, there was only a small increase in purity relative to the load. Thus, experiments employing $Ni^{++}$IMAC were conducted as the metal of choice. In these experiments, the CBS sample was run through a G-25 column to remove dithiothreitol (DTT) prior to loading the solution onto the IMAC column. Purity enhancement remained low and selectivity was similar to $Cu^{++}$, as evidenced by a relatively small $A_{280}$ peak in the high imidazole strip fraction. (FIGS. 8, 9 and 10).

Figure 7:
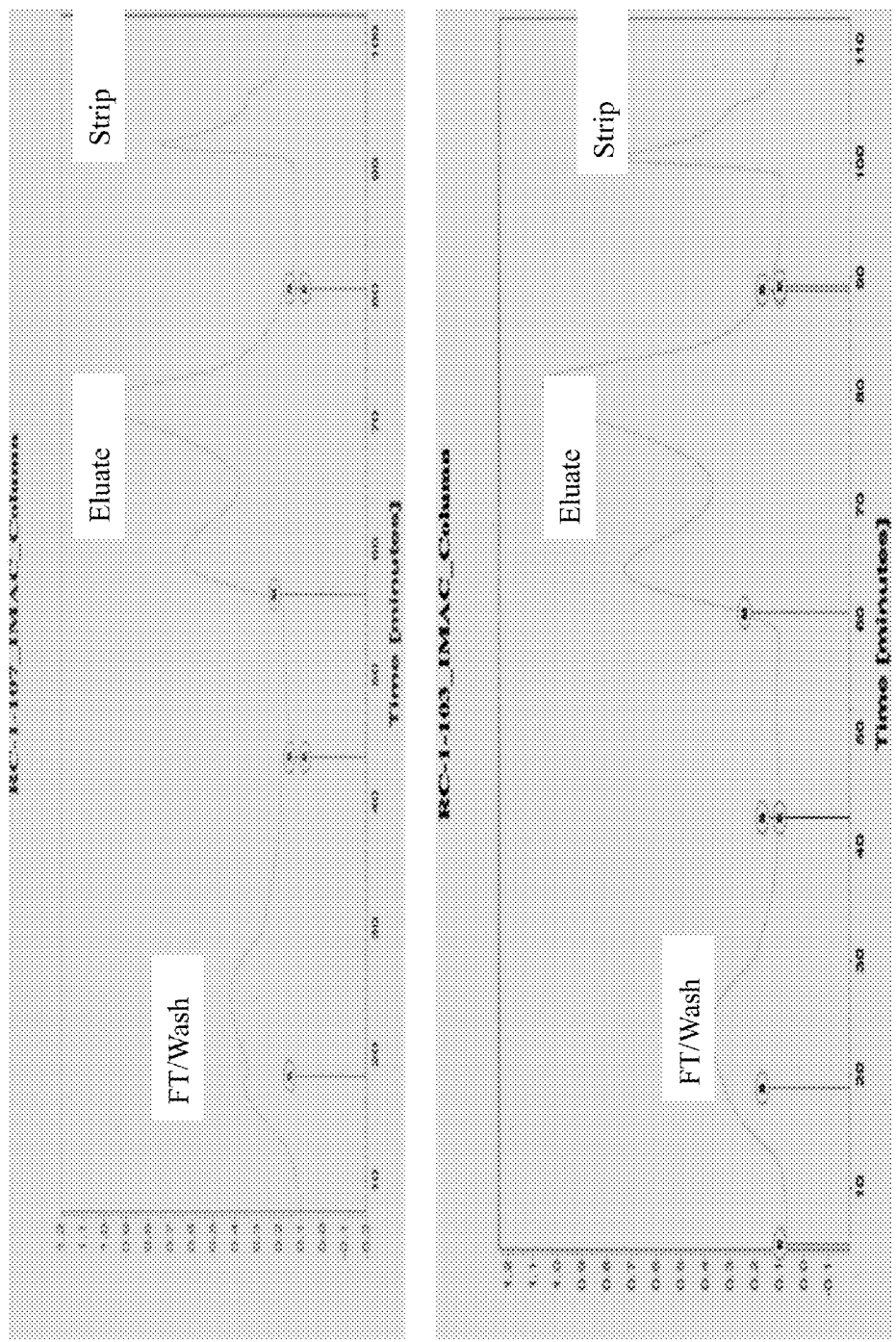
FIG. 7 is chromatograms demonstrating the components of the separated mixture following purification using Zn-IMAC.
Figure 13:
FIG. 13 is a photoimage of a SDS page gel showing the relative amounts of CBS protein and impurities for each stage of the purification step using a Zn-IMAC column.
Figure 14:
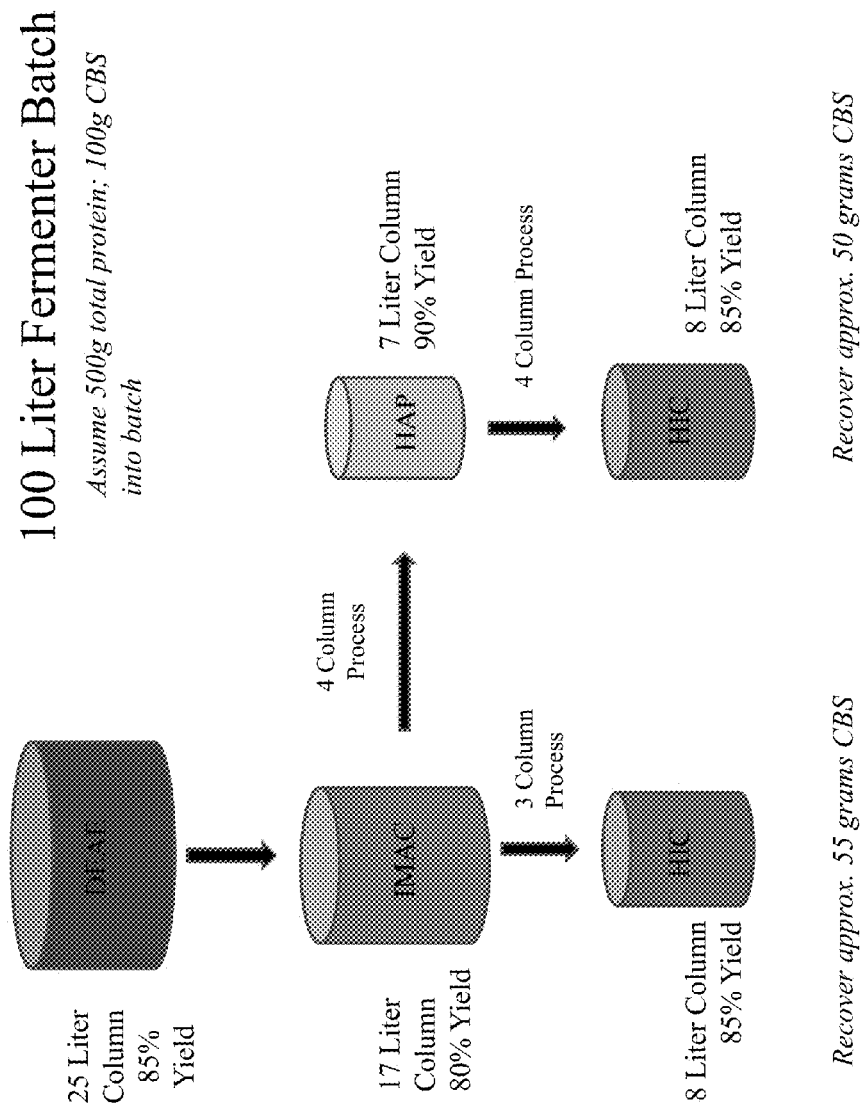
FIG. 14 is a scheme of the purification method using multi-step chromatography purification steps.

The relatively weak binding $Zn^{++}$ was also tested. Although capture, wash and elution conditions required significantly lower imidazole concentrations, potential for purity enhancement provided positive results due to the significant size of the $A_{280}$ peaks in the post-load wash and high imidazole strip fractions. 0.4 M NaCl and 0.01% Triton X-100 were added to the equilibration and wash buffers to minimize non-specific binding. (FIGS. 1 and 3). Samples were analyzed by SDS-PAGE to determine the relative amounts of CBS protein and impurities (FIG. 13). The results of the IMAC experiments are presented in FIG. 7. The following tables represent column operational parameters and data from the scale-up runs that employed them.

TABLE 3

Operational Parameters for Zn-IMAC Step

| Process Step | Column load target (total protein mg/mL) | Imidazole Concentration (with 20 mM $Na_3PO_4$ pH 7.0) | Column Volumes (mL) | Contact time Column vol./ flow rate (min.) |
|---|---|---|---|---|
| Equilibration | N/A | 1 mM | 3 | 10 |
| Load | 10 | 0 | Variable | 10 |
| Wash | N/A | 1 mM | 3 | 10 |
| Elution | N/A | 11 mM | Variable* | 10 |
| Strip | N/A | 100 mM | 3 | 10 |

*Note: Eluate collection starts at approx. 0.25 AU and ends at approx. 0.16 AU. Void volume typically approx. 1.5 column volumes.

TABLE 4

Data from Scale-up Runs (n = 5)

| Input Column loading (per mL Resin) | | Output | | |
|---|---|---|---|---|
| Total Protein (mg) | Units | Recovery (%) | Fold Purif. (By S.A.) | |
| 6.5-9.3 | 4414-7038 | 71.8-84.6 | 1.3-1.6 | Range |
| 8.1 | 5687 | 80 | 1.4 | Average |

Example 5

HIC Chromatography

Multiple experiments were conducted to identify the parameters for HIC chromatography. Initial drip column experiments were conducted that employed a resin with a relatively strong binding ligand (phenyl) with an IMAC eluate as starting material/load. This experiment resulted in empirically complete binding at 1.3M $(NH_4)_2SO_4$. However, there was evidence of significant retention of CBS on the column even after washing with a low ionic strength buffer. Based on these results, a resin with a weaker binding ligand (butyl) was tested. Initial experiments with this resin showed no apparent capture at 0.5M $(NH_4)_2SO_4$. The non-binding flow through of this column experiment was collected and adjusted to 1.25M $(NH_4)_2SO_4$, and reloaded on to a column equilibrated to the same concentration of $(NH_4)_2SO_4$. In this case there was evidence of significant binding to the column. A 20 column volume $(NH_4)_2SO_4$ gradient elution was performed from 1.25M to 0.25M $(NH_4)_2SO_4$ with fractions collected. SDS-PAGE analysis of the fractions indicated that there was significant potential for impurity clearance on the lower end of the gradient. Experiments utilizing step gradient washes at varying concentrations of $(NH_4)_2SO_4$ determined the final operational parameters. (FIGS. 1 and 3). Those parameters and the scale-up run data are summarized in the tables below.

TABLE 5

Operational parameters for HIC Step (n = 6)

| Process Step | Column load target (total protein mg/mL) | $(NH_4)_2SO_4$ Concentration (with 20 mM $Na_3PO_4$ pH 7.0) | Column Volumes (mL) | Contact time Column vol./ flow rate (min.) |
|---|---|---|---|---|
| Equilibration | N/A | 1.4M | 3 | 10 |
| Load | 5-10 | 1.4M | Variable | 10 |
| Wash | N/A | 1.4M | 3 | 10 |
| Elution | N/A | 1.1M | Variable* | 10 |
| Strip | N/A | 0.05M NaCl | 3 | 10 |

*Note: Eluate collection starts at approx. 0.25 AU and ends at approx. 0.15 AU. Void volume typically approx. 1.4 column volumes.

TABLE 6

Data from Scale-up Runs (n = 5)

| Input Column loading (per mL Resin) | | Output | | |
|---|---|---|---|---|
| Total Protein (mg) | Units | Recovery (%) | Fold Purif. (By S.A.) | |
| 5.1-7.2 | 5375-9248 | 77.8-92.7 | 1.0-1.3 | Range |
| 6.3 | 7638 | 85 | 1.2 | Average |

Example 6

CHAP Chromatography

Ceramic hydroxyapatite is a resin that has a unique, potentially mixed binding mode chemistry that was utilized in a CBS purification method. CBS displayed acidic characteristics and therefore initial investigation focused on using phosphate-modulated partitioning. The initial experiments utilized HIC eluate that was buffer exchanged into a 0.05M NaCl, 0.005M Potassium Phosphate (pH 6.8) buffer. A 5 mL ceramic hydroxyapatite (Type 1) cartridge was equilibrated in the same buffer and the conditioned HIC eluate was loaded onto the column. There was no visible breakthrough of protein (as measured by $A_{280}$) during the load and subsequent wash with equilibration/wash buffer. A linear gradient (5%) of 0.005M to 0.5M Potassium Phosphate was then run and fractions were collected. Based on the chromatogram, samples were analyzed by SDS-PAGE to determine the relative amounts of CBS protein and impurities. In subsequent experiments (based on analysis of the results of previous experiments), step washes with varying levels of phosphate were employed to determine optimal conditions for load, wash, and elution steps. In addition, the composition of buffer salts was transitioned from Potassium to Sodium Phosphate. (FIG. 3). The following tables represent column operational parameters and data from the scale-up runs that employed them.

TABLE 7

Operational Parameters for CHAP Step

| Process Step | Column load target (total protein mg/mL) | Na$_3$PO$_4$ Concentration (with 50 mM NaCl, pH 7.0) | Column Volumes (mL) | Contact time Column vol./flow rate (min.) |
|---|---|---|---|---|
| Equilibration | N/A | 10 mM | 3 | 6 |
| Load | 10-15 | 10 mM | Variable | 6 |
| Wash | N/A | 30 mM | 3 | 6 |
| Elution | N/A | 90 mM | Variable* | 6 |
| Strip | N/A | 150 mM | 3 | 6 |

*Note: Eluate collection starts at approx. 0.20 AU and ends at approx. 0.16 AU. Void volume typically approx. 1.0 column volumes.

TABLE 8

Data from Scale-up Runs (n = 5)

| Input Column loading (per mL Resin) | | Output | | |
|---|---|---|---|---|
| Total Protein (mg) | Units | Recovery (%) | Fold Purif. (By S.A.) | |
| 9.9-12.2 | 11205-12297 | 84.6-92.4 | 1.1-1.2 | Range |
| 11.1 | 11751 | 89 | 1.2 | Average |

Example 7

Integrated Process Results

Figure 5:
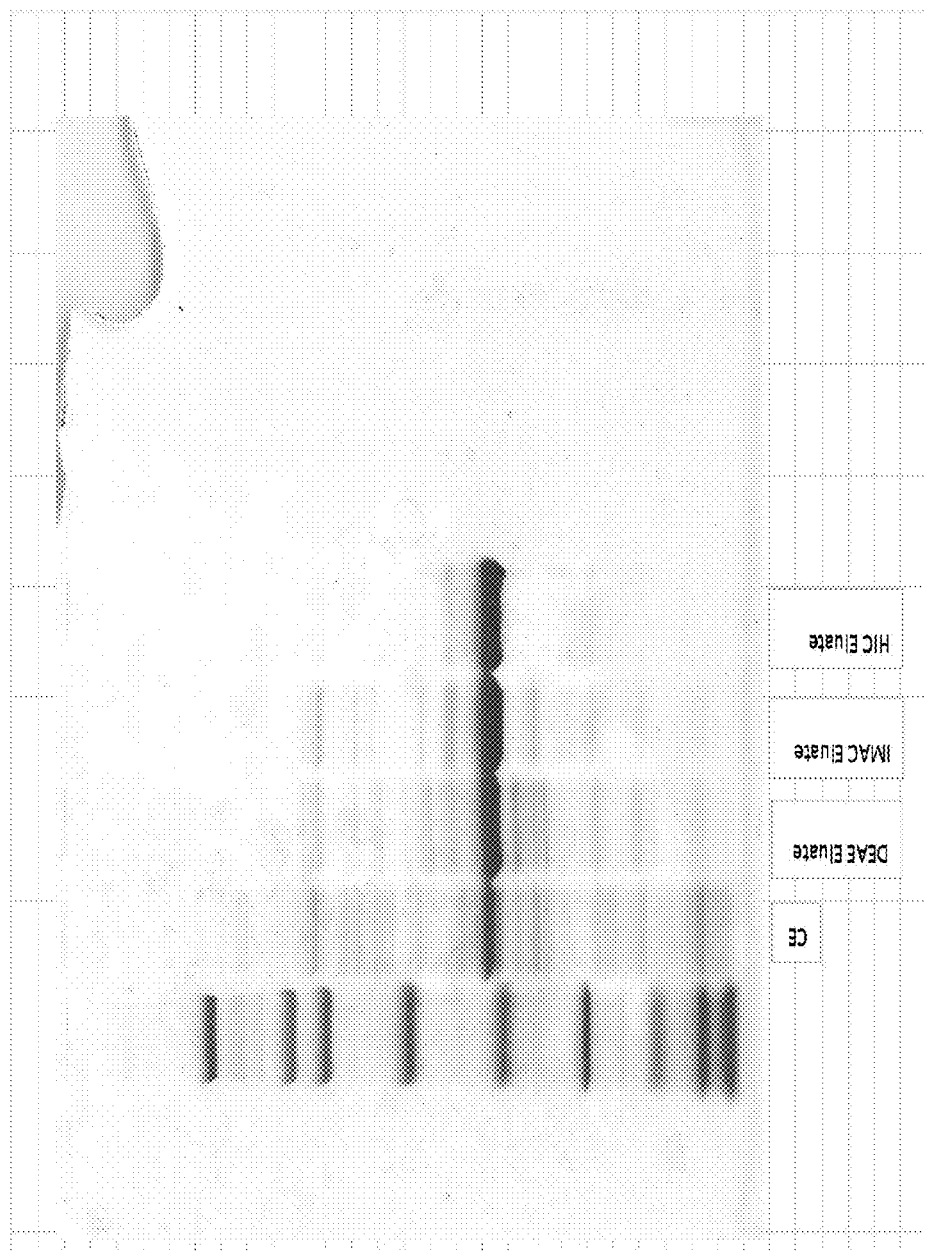
FIG. 5 is a photoimage of a SDS page gel showing the relative amounts of CBS protein and impurities for a 3 column purification method including: a DEAE column, a Zn-IMAC column and HIC column.
Figure 6:
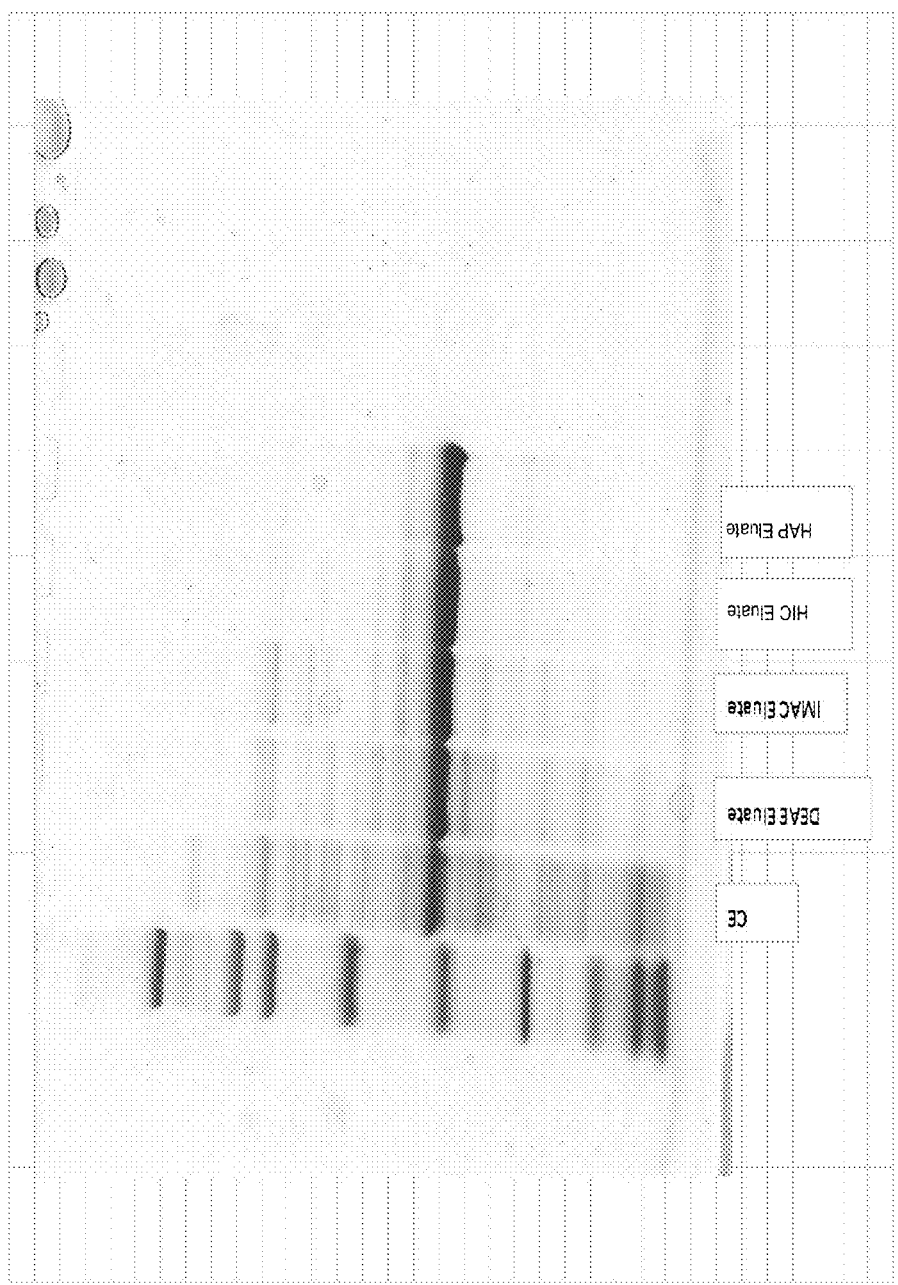
FIG. 6 is a photoimage of a SDS page gel showing the relative amounts of CBS protein and impurities for a 4 column purification method including: a DEAE column, a Zn-IMAC column, a ceramic hydroxyapaptite resin and a HIC column.

The particular multi-step method described in these Examples was evaluated at the scale of a 60 mL capture column. All of the purification trains utilized starting material (crude extract) obtained from fermentations that were seeded with recombinant cells comprising a construct comprising a truncated variant of human CBS encoded by a nucleic acid having codons optimized for expression in E. coli. This construct resulted in starting material that was approximately 2-fold higher in specific activity, and significantly impacted the final purity achieved from the integrated purification method. The overall purification results using the multi-step method were measured by SDS-PAGE and Specific Activity (FIGS. 5 and 6). The results demonstrated that the purity and specific activity met or exceeded that of the purified tagged truncated CBS. All Specific Activities of final column eluates obtained by the largest scale currently possible exceeded 1200 U/mg total protein. The following table summarizes the overall purification results from the scale-up runs.

TABLE 9

Overall Results from Scale-Up Runs

| | Total Recovery (%) | | Fold Purification | |
|---|---|---|---|---|
| | Range | Average | Range | Average |
| 3 Column Train (n = 3) | 57-60 | 58 | 5.7-6.2 | 5.9 |
| 4 Column Train (n = 2) | 47-52 | 50 | 4.6-5.4 | 5.0 |

Specific Activity of Final Column Eluate = 1206-1509.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 10

CβS Sequences

| Molecule | SEQ ID NO | Sequence |
|---|---|---|
| Native human CβS nucleic acid sequence | 1 | atgccttctgagacccccaggcagaagtggggcccacag gctgccccaccgctcagggccacactcggcgaaggggag cctggagaaggggtccccagaggataaggaagccaaggag cccctgtggatccggcccgatgctccgagcaggtgcacct ggcagctgggccggcctgcctccgagtccccacatcacca cactgccccggcaaaatctccaaaaatcttgccagatatt ctgaagaaaatcggggacacccctatggtcagaatcaaca agattgggaagaagttcggcctgaagtgtgagctcttggc caagtgtgagttcttcaacgcgggcgggagcgtgaaggac cgcatcagcctgcggatgattgaggatgctgagcgcgacg ggacgctgaagcccggggacacgattatcgagccgacatc cgggaacaccgggatcgggctggccctggctgcggcagtg aggggctatcgctgcatcatcgtgatgccagagaagatga gctccgagaaggtggacgtgctgcgggcactgggggctga gattgtgaggacgccaccaatgccaggttcgactccccg gagtcacacgtgggggtggcctggcggctgaagaacgaaa tccccaattctcacatcctagaccagtaccgcaacgccag caaccccctggctcactacgacaccaccgctgatgagatc ctgcagcagtgtgatgggaagctggacatgctggtggctt cagtgggcacgggcggcaccatcacgggcattgccaggaa gctgaaggagaagtgtcctggatgcaggatcattggggtg gatcccgaagggtccatcctcgcagagccggaggagctga accagacggagcagacaacctacgaggtggaagggatcgg |

TABLE 10-continued

CβS Sequences

| Molecule | SEQ ID NO | Sequence |
|---|---|---|
| | | ctacgacttcatccccacggtgctggacaggacggtggtg<br>gacaagtggttcaagagcaacgatgaggaggcgttcacct<br>tgcccgcatgctgatcgcgcaagaggggctgctgtgcgg<br>tggcagtgctggcagcacggtggcggtggccgtgaaggct<br>gcgcaggagctgcaggagggccagcgctgcgtggtcattc<br>tgcccgactcagtgcggaactacatgaccaagttcctgag<br>cgacaggtggatgctgcagaagggctttctgaaggaggag<br>gacctcacggagaagaagcccgtggtggcacctccgtg<br>ttcaggagctgggcctgtcagccccgctgaccgtgctccc<br>gaccatcacctgtgggcacaccatcgagatcctccgggag<br>aagggcttcgaccaggcgcccgtggtggatgaggcgggg<br>taatcctgggaatggtgacgcttgggaacatgctctcgtc<br>cctgcttgccgggaaggtgcagccgtcagaccaagttggc<br>aaagtcatctacaagcagttcaaacagatccgcctcacgg<br>acacgctgggcaggctctcgcacatcctggagatggacca<br>cttcgccctggtggtgcacgagcagatccagtaccacagc<br>accgggaagtccagtcagcggcagatggtgttcggggtgg<br>tcaccgccattgacttgctgaacttcgtggccgcccagga<br>gcgggaccagaagtga |
| Native human CβS polypeptide sequence | 2 | MPSETPQAEVGPTGCPHRSGPHSAKGSLEKGSPEDKEAKE<br>PLWIRPDAPSRCTWQLGRPASESPHHHTAPAKSPKILPDI<br>LKKIGDTPMVRINKIGKKFGLKCELLAKCEFFNAGGSVKD<br>RISLRMIEDAERDGTLKPGDTIIEPTSGNTGIGLALAAAV<br>RGYRCIIVMPEKMSSEKVDVLRALGAEIVRTPTNARFDSP<br>ESHVGVAWRLKNEIPNSHILDQYRNASNPLAHYDTTADEI<br>LQQCDGKLDMLVASVGTGGTITGIARKLKEKCPGCRIIGV<br>DPEGSILAEPEELNQTEQTTYEVEGIGYDFIPTVLDRTVV<br>DKWFKSNDEEAFTFARMLIAQEGLLCGGSAGSTVAVAVKA<br>AQELQEGQRCVVILPDSVRNYMTKFLSDRWMLQKGFLKEE<br>DLTEKKPWWWHLRVQELGLSAPLTVLPTITCGHTIEILRE<br>KGFDQAPVVDEAGVILGMVTLGNMLSSLLAGKVQPSDQVG<br>KVIYKQFKQIRLTDTLGRLSHILEMDHFALVVHEQIQYHS<br>TGKSSQRQMVFGVVTAIDLLNFVAAQERDQK |
| Truncated, Human CβS polypeptide sequence | 3 | MPSETPQAEVGPTGCPHRSGPHSAKGSLEKGSPED<br>KEAKEPLWIRPDAPSRCTWQLGRPASESPHHHTAP<br>AKSPKILPDILKKIGDTPMVRINKIGKKFGLKCEL<br>LAKCEFFNAGGSVKDRISLRMIEDAERDGTLKPGD<br>TIIEPTSGNTGIGLALAAAVRGYRCIIVMPEKMSS<br>EKVDVLRALGAEIVRTPTNARFDSPESHVGVAWRL<br>KNEIPNSHILDQYRNASNPLAHYDTTADEILQQCD<br>GKLDMLVASVGTGGTITGIARKLKEKCPGCRIIGV<br>DPEGSILAEPEELNQTEQTTYEVEGIGYDFIPTVL<br>DRTVVDKWFKSNDEEAFTFARMLIAQEGLLCGGSA<br>GSTVAVAVKAAQELQEGQRCVVILPDSVRNYMTKF<br>LSDRWMLQKGFLKEEDLTEKKPWWWHLR |
| Truncated, Optimized Human CβS nucleic acid sequence | 4 | ATGCCGTCAGAAACCCCGCAGGCAGAAGTGGGTCCGACGG<br>GTTGCCCGCACCGTAGCGGTCCGCATTCTGCAAAAGGCAG<br>TCTGGAAAAAGGTTCCCCGGAAGATAAAGAAGCCAAAGAA<br>CCGCTGTGGATTCGTCCGGACGCACCGTCACGCTGTACCT<br>GGCAGCTGGGTCGTCCGGCAAGCGAATCTCCGCATCACCA<br>TACGGCTCCGGCGAAAAGTCCGAAAATTCTGCCGGATATC<br>CTGAAGAAAATTGGTGACACCCCGATGGTTCGTATCAACA<br>AAATCGGCAAAAAATTCGGTCTGAAATGCGAACTGCTGGC<br>TAAATGTGAATTTTTCAATGCGGGCGGTTCCGTGAAAGAT<br>CGTATCTCACTGCGCATGATTGAAGATGCTGAACGCGACG<br>GCACCCTGAAACCGGGTGATACGATTATCGAACCGACCTC<br>TGGCAACACGGGTATCGGTCTGGCACTGGCGGCGGCAGTC<br>CGTGGTTATCGCTGCATTATCGTGATGCCGGAAAAAATGA<br>GCTCTGAAAAGTTGATGTCCTGCGTGCTCTGGGCGCGGA<br>AATTGTTCGTACCCCGACGAATGCCCGCTTCGACAGTCCG<br>GAATCCCATGTGGGTGTTGCATGGCGCCTGAAAAACGAAA<br>TCCCGAATTCGCACATTCTGGATCAGTATCGTAACGCTAG<br>CAATCCGCTGGCGCATTACGATACCACGGCCGACGAAATC<br>CTGCAGCAATGTGATGGCAAACTGGACATGCTGGTCGCTT<br>CTGTGGGTACCGGCGGTACCATTACGGGCATCGCGCGTAA<br>ACTGAAAGAAAAATGCCCGGGCTGTCGCATTATCGGTGTG<br>GATCCGGAAGGCAGTATTCTGGCGGAACCGGAAGAACTGA<br>ACCAGACCGAACAAACCACGTATGAAGTTGAAGGCATCGG<br>TTACGATTTTATTCCGACCGTCCTGGATCGCACGGTGGTT<br>GACAAATGGTTCAAAGCAATGACGAAGAAGCCTTTACCT<br>TCGCACGTATGCTGATCGCTCAGGAAGGTCTGCTGTGCGG<br>TGGTTCAGCAGGTTCGACGGTCGCAGTGGCAGTTAAAGCT<br>GCGCAGGAACTGCAAGAAGGTCAACGTTGTGTCGTGATTC |

TABLE 10-continued

| CβS Sequences | | |
|---|---|---|
| Molecule | SEQ ID NO | Sequence |
| | | TGCCGGATTCTGTTCGCAACTACATGACCAAATTTCTGAG
TGACCGTTGGATGCTGCAAAAAGGCTTCCTGAAAGAAGAA
GATCTGACCGAGAAAAAACCGTGGTGGTGGCACCTGCGCT
AA |

The invention claimed is:

1. A method for purifying cystathionine β-synthase (CBS) protein, wherein the CBS protein is the CBS protein of SEQ ID NO: 02, or a truncation thereof, the method comprising the steps of:
   (a) providing a CBS-containing solution comprising one or a plurality of impurities; and
   (b) first performing chromatographic separation of the CBS-containing solution using an ion exchange chromatography column; and
   (c) second performing a chromatographic separation using a metal affinity chromatography (IMAC) resin, wherein the impurities are removed thereby.

2. The method of claim 1, further comprising the step of performing chromatographic separation using a Hydrophobic Interaction Chromatography (HIC) column.

3. The method of claim 1, further comprising the step of performing chromatographic separation using a ceramic hydroxyapatite resin.

4. The method of claim 1, wherein the ion exchange chromatography column is a weak anion exchanger.

5. The method of claim 4, wherein the weak anion exchanger is a DEAE-Sepharose FF column.

6. The method of claim 1, wherein the metal affinity chromatography (IMAC) resin is charged with a divalent metal cation.

7. The method of claim 6, wherein the divalent metal cation is nickel, copper, cobalt or zinc.

8. The method of claim 7, wherein the divalent metal ion is zinc.

9. The method of claim 1, further comprising eluting CBS from the metal affinity chromatography (IMAC) resin with an elution buffer comprising imidazole.

10. The method of claim 1, wherein the truncated CBS protein has an amino acid sequence identified by SEQ ID NO: 3.

11. The method of claim 1, wherein the CBS-containing solution is a clarified CBS solution.

12. The method of claim 1, wherein the CBS is produced in a recombinant cell.

13. The method of claim 12, wherein the recombinant cell is a bacterial cell.

14. The method of claim 13, wherein the CBS-containing solution is obtained by homogenizing recombinant bacterial cells expressing a recombinant construct comprising a nucleic acid sequence encoding CBS.

15. The method of claim 14, wherein the CBS nucleic acid encodes a truncated CBS protein.

16. The method of claim 15, wherein the truncated CBS protein has been truncated to an ending position of one of amino acid residues from 382-532, 382-550 or 543-550 of SEQ ID NO:2.

17. The method of claim 16, wherein the CBS nucleic acid sequence comprises SEQ ID NO. 4.

18. The method of claim 16, wherein the nucleic acid sequence encoding the truncated CBS protein is optimized for expression in E. coli cells.

19. The method of claim 12, wherein the recombinant cells are E. coli cells.

* * * * *

SEQUENCE LISTING

<160> NUMBER OF SEQ ID NOS: 6

<210> SEQ ID NO 1
<211> LENGTH: 1656
<212> TYPE: DNA
<213> ORGANISM: Homo sapiens

<400> SEQUENCE: 1

```
atgccttctg agacccccca ggcagaagtg gggcccacag gctgccccca ccgctcaggg      60
ccacactcgg cgaaggggag cctggagaag gggtccccag aggataagga agccaaggag     120
cccctgtgga tccggcccga tgctccgagc aggtgcacct ggcagctggg ccggcctgcc     180
tccgagtccc cacatcacca cactgccccg gcaaaatctc caaaaatctt gccagatatt     240
ctgaagaaaa tcgggacac ccctatggtc agaatcaaca agattgggaa gaagttcggc      300
ctgaagtgtg agctcttggc caagtgtgag ttcttcaacg cggcgggag cgtgaaggac      360
cgcatcagcc tgcggatgat tgaggatgct gagcgcgacg ggacgctgaa gcccggggac      420
acgattatcg agccgacatc cgggaacacc gggatcgggc tggccctggc tgcggcagtg      480
agggctatc gctgcatcat cgtgatgcca gagaagatga gctccgagaa ggtggacgtg      540
ctgcgggcac tggggctga gattgtgagg acgcccacca atgccaggtt cgactccccg      600
gagtcacacg tggggtggc ctggcggctg aagaacgaaa tccccaattc tcacatccta      660
gaccagtacc gcaacgccag caacccctg gctcactacg acaccaccgc tgatgagatc      720
ctgcagcagt gtgatgggaa gctggacatg ctggtggctt cagtgggcac gggcggcacc      780
atcacgggca ttgccaggaa gctgaaggag aagtgtcctg atgcaggat cattggggtg      840
gatcccgaag gtccatcct cgcagagccg gaggagctga accagacgga gcagacaacc      900
tacgaggtgg aagggatcgg ctacgacttc atccccacgg tgctggacag gacggtggtg      960
gacaagtggt tcaagagcaa cgatgaggag gcgttcacct ttgcccgcat gctgatcgcg     1020
caagaggggc tgctgtgcgg tggcagtgct ggcagcacgg tggcggtggc cgtgaaggct     1080
gcgcaggagc tgcaggaggg ccagcgctgc gtggtcattc tgcccgactc agtgcggaac     1140
tacatgacca gttcctgag cgacaggtgg atgctgcaga agggctttct gaaggaggag     1200
gacctcacgg agaagaagcc ctggtggtgg cacctccgtg ttcaggagct gggcctgtca     1260
gccccgctga ccgtgctccc gaccatcacc tgtgggcaca ccatcgagat cctccgggag     1320
aagggcttcg accaggcgcc cgtggtggat gaggcgggg taatcctggg aatggtgacg     1380
cttgggaaca tgctctcgtc cctgcttgcc gggaaggtgc agccgtcaga ccaagttggc     1440
aaagtcatct acaagcagtt caaacagatc cgcctcacgg acacgctggg caggctctcg     1500
cacatcctgg agatggacca cttcgccctg gtggtgcacg agcagatcca gtaccacagc     1560
accgggaagt ccagtcagcg gcagatggtg ttcggggtgg tcaccgccat tgacttgctg     1620
aacttcgtgg ccgcccagga gcgggaccag aagtga                               1656
```

<210> SEQ ID NO 2
<211> LENGTH: 551
<212> TYPE: PRT
<213> ORGANISM: Homo sapiens

<400> SEQUENCE: 2

```
Met Pro Ser Glu Thr Pro Gln Ala Glu Val Gly Pro Thr Gly Cys Pro
  1               5                  10                  15

His Arg Ser Gly Pro His Ser Ala Lys Gly Ser Leu Glu Lys Gly Ser
             20                  25                  30

Pro Glu Asp Lys Glu Ala Lys Glu Pro Leu Trp Ile Arg Pro Asp Ala
         35                  40                  45

Pro Ser Arg Cys Thr Trp Gln Leu Gly Arg Pro Ala Ser Glu Ser Pro
     50                  55                  60

His His His Thr Ala Pro Ala Lys Ser Pro Lys Ile Leu Pro Asp Ile
 65                  70                  75                  80

Leu Lys Lys Ile Gly Asp Thr Pro Met Val Arg Ile Asn Lys Ile Gly
                 85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
```

```
                  370                 375                 380
Phe Leu Ser Asp Arg Trp Met Leu Gln Lys Gly Phe Leu Lys Glu Glu
385                 390                 395                 400

Asp Leu Thr Glu Lys Lys Pro Trp Trp His Leu Arg Val Gln Glu
            405                 410                 415

Leu Gly Leu Ser Ala Pro Leu Thr Val Leu Pro Thr Ile Thr Cys Gly
            420                 425                 430

His Thr Ile Glu Ile Leu Arg Glu Lys Gly Phe Asp Gln Ala Pro Val
            435                 440                 445

Val Asp Glu Ala Gly Val Ile Leu Gly Met Val Thr Leu Gly Asn Met
450                 455                 460

Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
            515                 520                 525

Met Val Phe Gly Val Val Thr Ala Ile Asp Leu Leu Asn Phe Val Ala
            530                 535                 540

Ala Gln Glu Arg Asp Gln Lys
545                 550

<210> SEQ ID NO 3
<211> LENGTH: 413
<212> TYPE: PRT
<213> ORGANISM: Artificial Sequence
<220> FEATURE:
<223> OTHER INFORMATION: Synthetic

<400> SEQUENCE: 3

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
            115                 120                 125

Asp Ala Glu Arg Asp Gly Thr Leu Lys Pro Gly Asp Thr Ile Ile Glu
        130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
```

```
                180             185             190
Thr Asn Ala Arg Phe Asp Ser Pro Glu Ser His Val Gly Val Ala Trp
            195                 200                 205
Arg Leu Lys Asn Glu Ile Pro Asn Ser His Ile Leu Asp Gln Tyr Arg
        210                 215                 220
Asn Ala Ser Asn Pro Leu Ala His Tyr Asp Thr Ala Asp Glu Ile
225                 230                 235                 240
Leu Gln Gln Cys Asp Gly Lys Leu Asp Met Leu Val Ala Ser Val Gly
                245                 250                 255
Thr Gly Gly Thr Ile Thr Gly Ile Ala Arg Lys Leu Lys Glu Lys Cys
            260                 265                 270
Pro Gly Cys Arg Ile Ile Gly Val Asp Pro Glu Gly Ser Ile Leu Ala
        275                 280                 285
Glu Pro Glu Glu Leu Asn Gln Thr Glu Gln Thr Thr Tyr Glu Val Glu
    290                 295                 300
Gly Ile Gly Tyr Asp Phe Ile Pro Thr Val Leu Asp Arg Thr Val Val
305                 310                 315                 320
Asp Lys Trp Phe Lys Ser Asn Asp Glu Glu Ala Phe Thr Phe Ala Arg
                325                 330                 335
Met Leu Ile Ala Gln Glu Gly Leu Leu Cys Gly Ser Ala Gly Ser
            340                 345                 350
Thr Val Ala Val Ala Val Lys Ala Ala Gln Glu Leu Gln Glu Gly Gln
        355                 360                 365
Arg Cys Val Val Ile Leu Pro Asp Ser Val Arg Asn Tyr Met Thr Lys
    370                 375                 380
Phe Leu Ser Asp Arg Trp Met Leu Gln Lys Gly Phe Leu Lys Glu Glu
385                 390                 395                 400
Asp Leu Thr Glu Lys Lys Pro Trp Trp Trp His Leu Arg
                405                 410
```

<210> SEQ ID NO 4
<211> LENGTH: 1242
<212> TYPE: DNA
<213> ORGANISM: Artificial Sequence
<220> FEATURE:
<223> OTHER INFORMATION: Synthetic

<400> SEQUENCE: 4

| | | | | | |
|---|---|---|---|---|---|
| atgccgtcag | aaaccccgca | ggcagaagtg | ggtccgacgg | gttgcccgca | ccgtagcggt | 60 |
| ccgcattctg | caaaaggcag | tctggaaaaa | ggttccccgg | aagataaaga | agccaaagaa | 120 |
| ccgctgtgga | ttcgtccgga | cgcaccgtca | cgctgtacct | ggcagctggg | tcgtccggca | 180 |
| agcgaatctc | cgcatcacca | tacggctccg | gcgaaaagtc | cgaaaattct | gccggatatc | 240 |
| ctgaagaaaa | ttggtgacac | cccgatggtt | cgtatcaaca | aaatcggcaa | aaaattcggt | 300 |
| ctgaaatgcg | aactgctggc | taaatgtgaa | tttttcaatg | cgggcggttc | cgtgaaagat | 360 |
| cgtatctcac | tgcgcatgat | tgaagatgct | gaacgcgacg | gcaccctgaa | accgggtgat | 420 |
| acgattatcg | aaccgaccct | ctggcaacac | ggtatcggtc | tggcactggc | ggcggcagtc | 480 |
| cgtggttatc | gctgcattat | cgtgatgccg | gaaaaaatga | gctctgaaaa | agttgatgtc | 540 |
| ctgcgtgctc | tgggcgcgga | aattgttcgt | accccgacga | atgcccgctt | cgacagtccg | 600 |
| gaatcccatg | tgggtgttgc | atggcgcctg | aaaaacgaaa | tcccgaattc | gcacattctg | 660 |
| gatcagtatc | gtaacgctag | caatccgctg | gcgcattacg | ataccaccgc | cgacgaaatc | 720 |
| ctgcagcaat | gtgatggcaa | actggacatg | ctggtcgctt | ctgtgggtac | cggcggtacc | 780 |

```
attacgggca tcgcgcgtaa actgaaagaa aaatgcccgg gctgtcgcat tatcggtgtg      840
gatccggaag gcagtattct ggcggaaccg gaagaactga accagaccga acaaaccacg      900
tatgaagttg aaggcatcgg ttacgatttt attccgaccg tcctggatcg cacggtggtt      960
gacaaatggt tcaaaagcaa tgacgaagaa gcctttacct tcgcacgtat gctgatcgct     1020
caggaaggtc tgctgtgcgg tggttcagca ggttcgacgg tcgcagtggc agttaaagct     1080
gcgcaggaac tgcaagaagg tcaacgttgt gtcgtgattc tgccggattc tgttcgcaac     1140
tacatgacca aatttctgag tgaccgttgg atgctgcaaa aaggcttcct gaaagaagaa     1200
gatctgaccg agaaaaaacc gtggtggtgg cacctgcgct aa                       1242

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
cgtagaattc acctttgccc gcatgctgat                                       30

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 6
tacgggtacc tcaacggagg tgccaccacc agggc                                 35
```